US011278446B2

(12) United States Patent
Rapoport

(10) Patent No.: US 11,278,446 B2
(45) Date of Patent: Mar. 22, 2022

(54) ACTIVE THERMO-REGULATED NEONATAL TRANSPORTABLE INCUBATOR

(71) Applicant: Aspect Imaging Ltd., Shoham (IL)

(72) Inventor: Uri Rapoport, Moshav Ben Shemen (IL)

(73) Assignee: ASPECT IMAGING LTD., Shoham (IL)

( * ) Notice: Subject to any disclaimer, the term of this patent is extended or adjusted under 35 U.S.C. 154(b) by 0 days.

(21) Appl. No.: 14/915,907

(22) PCT Filed: Sep. 2, 2014

(86) PCT No.: PCT/IL2014/050787
§ 371 (c)(1),
(2) Date: Mar. 2, 2016

(87) PCT Pub. No.: WO2015/029046
PCT Pub. Date: Mar. 5, 2015

(65) Prior Publication Data
US 2016/0206471 A1    Jul. 21, 2016

Related U.S. Application Data

(60) Provisional application No. 61/902,314, filed on Nov. 11, 2013, provisional application No. 61/902,236, (Continued)

(51) Int. Cl.
*A61F 7/00* (2006.01)
*A61G 11/00* (2006.01)
(Continued)

(52) U.S. Cl.
CPC ............ *A61F 7/0053* (2013.01); *A61G 11/00* (2013.01); *A61M 16/0003* (2014.02);
(Continued)

(58) Field of Classification Search
CPC ...................... A61G 11/00–009; A61F 7/0053
See application file for complete search history.

(56) References Cited

U.S. PATENT DOCUMENTS

| 1,900,342 A | 3/1933 | Hess |
| 2,401,605 A | 6/1946 | Boren |

(Continued)

FOREIGN PATENT DOCUMENTS

| CA | 2815746 | 5/2012 |
| CN | 2448344 | 9/2001 |

(Continued)

OTHER PUBLICATIONS

Antonucci, et al., The infant incubator in the neonatal intensive care unit: unresolved issues and future developments, J. Perinat. Med. 37(2009), 587-598.

(Continued)

*Primary Examiner* — Catherine B Kuhlman
(74) *Attorney, Agent, or Firm* — Loeb & Loeb LLP

(57) ABSTRACT

The present invention provides an elongated active thermo-regulated neonatal transportable incubator (ANTI), having a main longitudinal axis with a proximal end and an opposite distal end comprising adjacent to at least one of the ends a temperature regulating vent (TRV). The TRV is configured to stream air from one end towards the opposite end substantially along the axis, and the ANTI is configured, by means of size and shape, to accommodate the neonate in parallel to the axis. Further the ANTI can be configured by means of size shape and material to at least partially inserted into an MRD having an open bore in its longitudinal axis, further accommodating the neonate parallel to the MRD bore. An incubator with a temperature regulating vent located outside the incubator and its base.

16 Claims, 18 Drawing Sheets

Related U.S. Application Data filed on Nov. 10, 2013, provisional application No. 61/893,959, filed on Oct. 22, 2013, provisional application No. 61/879,154, filed on Sep. 18, 2013, provisional application No. 61/872,793, filed on Sep. 2, 2013.

(51) Int. Cl.

| | | |
|---|---|---|
| *G10K 11/162* | (2006.01) | |
| *G10K 11/175* | (2006.01) | |
| *A61M 16/16* | (2006.01) | |
| *A61M 16/10* | (2006.01) | |
| *A61M 16/00* | (2006.01) | |
| *G01H 3/14* | (2006.01) | |
| *G10K 11/168* | (2006.01) | |
| *G10K 11/172* | (2006.01) | |
| *G10K 11/20* | (2006.01) | |
| *A61B 5/055* | (2006.01) | |

(52) U.S. Cl.
CPC ........ *A61M 16/105* (2013.01); *A61M 16/161* (2014.02); *G10K 11/162* (2013.01); *G10K 11/175* (2013.01); *A61B 5/055* (2013.01); *A61B 2503/045* (2013.01); *A61F 2007/006* (2013.01); *A61F 2007/0054* (2013.01); *A61F 2007/0055* (2013.01); *A61F 2007/0057* (2013.01); *A61F 2007/0093* (2013.01); *A61F 2007/0095* (2013.01); *A61G 11/009* (2013.01); *A61G 2200/14* (2013.01); *A61G 2203/30* (2013.01); *A61G 2203/36* (2013.01); *A61G 2203/44* (2013.01); *A61G 2203/46* (2013.01); *A61G 2203/70* (2013.01); *A61G 2210/50* (2013.01); *A61M 2016/0027* (2013.01); *A61M 2205/0233* (2013.01); *A61M 2205/3633* (2013.01); *A61M 2205/42* (2013.01); *G01H 3/14* (2013.01); *G10K 11/168* (2013.01); *G10K 11/172* (2013.01); *G10K 11/20* (2013.01); *G10K 2210/116* (2013.01); *G10K 2210/118* (2013.01); *G10K 2210/129* (2013.01); *G10K 2210/301* (2013.01); *G10K 2210/3223* (2013.01); *G10K 2210/3224* (2013.01); *G10K 2210/509* (2013.01)

(56) References Cited

U.S. PATENT DOCUMENTS

| | | | |
|---|---|---|---|
| 2,633,842 A | 4/1953 | Higgs | |
| 2,638,087 A | 5/1953 | Livsey et al. | |
| 2,708,927 A | 5/1955 | Dixon et al. | |
| 3,012,836 A | 12/1961 | Smith et al. | |
| 3,315,671 A | 4/1967 | Creelman | |
| 3,470,866 A | 10/1969 | Gittelson | |
| 3,655,178 A | 4/1972 | Vezina | |
| 3,710,791 A | 1/1973 | Deaton | |
| 3,920,000 A * | 11/1975 | Atherton | A61G 11/00 236/3 |
| 4,121,571 A * | 10/1978 | Pickering | A61G 11/00 128/204.17 |
| 4,161,172 A | 7/1979 | Pickering | |
| 4,509,505 A * | 4/1985 | Mercey | A61G 11/00 600/22 |
| 4,567,894 A | 2/1986 | Bergman | |
| 4,712,263 A | 12/1987 | Pronzinski | |
| 4,750,474 A | 6/1988 | Dukhan et al. | |
| 4,936,824 A | 6/1990 | Koch et al. | |
| 5,028,872 A | 7/1991 | Nakabayashi | |
| 5,059,906 A | 10/1991 | Yamanaka | |
| 5,100,375 A * | 3/1992 | Koch | A61G 11/00 600/22 |
| 5,446,934 A | 9/1995 | Frazier | |
| 5,509,159 A | 4/1996 | Du-Bois | |
| 5,534,669 A | 7/1996 | Schroeder et al. | |
| 5,759,149 A | 6/1998 | Goldberg et al. | |
| 5,797,833 A * | 8/1998 | Kobayashi | A61G 11/00 600/22 |
| 5,800,335 A | 9/1998 | Koch et al. | |
| 5,817,003 A | 10/1998 | Moll et al. | |
| 5,917,324 A | 6/1999 | Leussler | |
| 5,943,716 A | 8/1999 | Chu | |
| 5,971,913 A | 10/1999 | Newkirk et al. | |
| 6,036,634 A | 3/2000 | Goldberg et al. | |
| 6,155,970 A | 12/2000 | Dykes et al. | |
| 6,193,285 B1 | 2/2001 | Proctor | |
| 6,231,499 B1 * | 5/2001 | Jones | A61G 11/00 600/22 |
| D446,675 S | 8/2001 | Straub | |
| 6,317,618 B1 | 11/2001 | Livni et al. | |
| 6,409,654 B1 | 6/2002 | McClain et al. | |
| 6,433,548 B1 | 8/2002 | Furuta et al. | |
| 6,471,634 B1 | 10/2002 | Dykes et al. | |
| 6,511,414 B1 | 1/2003 | Hamsund | |
| 6,611,702 B2 | 8/2003 | Rohling et al. | |
| 6,641,521 B2 | 11/2003 | Kolarovic | |
| 6,666,816 B2 | 12/2003 | Mountain | |
| RE38,453 E | 3/2004 | Lessard et al. | |
| 6,776,527 B1 | 8/2004 | Tybinkowski et al. | |
| 6,860,272 B2 | 3/2005 | Carter et al. | |
| 6,992,486 B2 | 1/2006 | Srinivasan | |
| 7,255,671 B2 | 8/2007 | Boone et al. | |
| 7,278,962 B2 | 10/2007 | Lonneker-Lammers | |
| D567,948 S | 4/2008 | Tierney et al. | |
| 7,482,558 B2 | 1/2009 | Koch | |
| 7,599,728 B2 | 10/2009 | Feenan | |
| 7,719,279 B2 | 5/2010 | Rapoport | |
| 7,784,121 B2 | 8/2010 | Ahlman | |
| 8,034,007 B2 | 10/2011 | Avitable | |
| 8,147,396 B2 | 4/2012 | Srinivasan | |
| 8,461,841 B2 | 6/2013 | Rapoport et al. | |
| 9,974,705 B2 | 5/2018 | Rapoport | |
| 2001/0049465 A1 | 12/2001 | Goldberg et al. | |
| 2002/0072648 A1 | 6/2002 | Dykes et al. | |
| 2002/0123681 A1 | 9/2002 | Zuk | |
| 2002/0143233 A1 | 10/2002 | Donnelly et al. | |
| 2002/0173696 A1 | 11/2002 | Kolarovic et al. | |
| 2002/0173717 A1 | 11/2002 | Rohling et al. | |
| 2003/0088175 A1 | 5/2003 | Branch et al. | |
| 2004/0030241 A1 | 2/2004 | Green et al. | |
| 2004/0034273 A1 | 2/2004 | Boris | |
| 2004/0133064 A1 * | 7/2004 | Castillon Levano | A61G 11/00 600/22 |
| 2004/0186341 A1 | 9/2004 | McDermott | |
| 2004/0236174 A1 | 11/2004 | Boone et al. | |
| 2004/0236175 A1 | 11/2004 | Boone et al. | |
| 2005/0004422 A1 | 1/2005 | Caspary et al. | |
| 2005/0020906 A1 | 1/2005 | Seijger et al. | |
| 2005/0038314 A1 | 2/2005 | Falk | |
| 2005/0113668 A1 * | 5/2005 | Srinivasan | A61B 5/055 600/411 |
| 2006/0079730 A1 | 4/2006 | Getsla | |
| 2007/0151564 A1 * | 7/2007 | Sadir | A61G 11/00 128/205.26 |
| 2007/0232894 A1 | 10/2007 | Feenan | |
| 2008/0163425 A1 | 7/2008 | White | |
| 2009/0044335 A1 | 2/2009 | Brewin | |
| 2009/0443355 | 2/2009 | Brewin et al. | |
| 2009/0209846 A1 | 8/2009 | Bammer | |
| 2010/0004502 A1 | 1/2010 | Honma et al. | |
| 2010/0010599 A1 | 1/2010 | Chen et al. | |
| 2010/0168502 A1 | 7/2010 | Delaporte et al. | |
| 2010/0315085 A1 | 12/2010 | Brown | |
| 2011/0048424 A1 | 3/2011 | Radko | |
| 2011/0113555 A1 | 5/2011 | Smith | |
| 2011/0125010 A1 | 5/2011 | Vaquero Lopez et al. | |
| 2011/0160521 A1 * | 6/2011 | Khodak | A61G 11/00 600/22 |
| 2012/0071745 A1 | 3/2012 | Rapoport | |
| 2012/0078034 A1 | 3/2012 | Falk et al. | |
| 2012/0126814 A1 | 5/2012 | Fischer et al. | |

(56) References Cited

U.S. PATENT DOCUMENTS

| | | |
|---|---|---|
| 2012/0140899 A1 | 6/2012 | Bailey et al. |
| 2012/0247488 A1 | 10/2012 | Tonks |
| 2013/0025062 A1 | 1/2013 | Esch |
| 2013/0109956 A1 | 5/2013 | Rapoport |
| 2013/0150656 A1 | 6/2013 | Falk et al. |
| 2013/0204074 A1 | 8/2013 | Belval et al. |
| 2013/0204617 A1 | 8/2013 | Kuo et al. |
| 2013/0267765 A1 | 10/2013 | Rapoport |
| 2013/0334439 A1 | 12/2013 | Etters |
| 2014/0003614 A1 | 1/2014 | Levitov et al. |
| 2014/0051976 A1 | 2/2014 | Rapoport et al. |
| 2014/0078301 A1 | 3/2014 | Fazzi et al. |
| 2014/0098934 A1 | 4/2014 | Kondo |
| 2014/0099010 A1 | 4/2014 | Rapoport |
| 2014/0117989 A1 | 5/2014 | Rapoport |
| 2014/0354279 A1 | 12/2014 | Dumoulin et al. |
| 2014/0357981 A1 | 12/2014 | Dumoulin |
| 2014/0364722 A1 | 12/2014 | Dumoulin |
| 2015/0137812 A1 | 5/2015 | Rapoport |
| 2015/0141799 A1 | 5/2015 | Rapoport et al. |
| 2016/0030264 A1 | 2/2016 | Lehmann et al. |
| 2016/0081582 A1 | 3/2016 | Rapoport |

FOREIGN PATENT DOCUMENTS

| | | |
|---|---|---|
| CN | 102551719 A | 7/2012 |
| DE | 19617739 | 6/1997 |
| EP | 1132072 | 9/2001 |
| EP | 2581071 | 4/2013 |
| IL | 226488 | 11/2016 |
| JP | H09-285505 | 11/1997 |
| JP | 2000-350751 | 12/2000 |
| JP | 2001-520917 | 11/2001 |
| JP | 2004-041736 | 2/2004 |
| JP | 2004531313 | 10/2004 |
| JP | 2005514078 | 5/2005 |
| JP | 2007252741 | 10/2007 |
| JP | 2010178857 | 8/2010 |
| JP | 2016539683 | 11/2016 |
| WO | WO 98/48756 A1 | 11/1998 |
| WO | WO9921526 | 5/1999 |
| WO | WO2008137003 | 11/2008 |
| WO | WO2010054457 | 5/2010 |
| WO | WO2011109761 | 9/2011 |
| WO | WO2012143825 | 10/2012 |
| WO | WO2013115847 | 8/2013 |

OTHER PUBLICATIONS

Baby Pod II Infant Transport Device, Advance Healthcare Technology, brochure, pp. 1-6.

Baby Pod II Operation and Maintenance Manual, revision 5, Jan. 2011, pp. 1-11.

Ferris et al., The design of neonatal incubators: a systems-oriented, human centered approach, J. Perinatology, 2013, 33, S24-S31.

Kitterman et al., Catheterization of umbilical vessels in newborn infants, Pediatric Clinics of North America, vol. 17, No. 4, Nov. 1970, 895-912.

Paley et al., An MR-compatible neonatal incubator, The British Journal of Radiology, 85, 2012, 952-958.

American National Standard, Medical Electrical Equipment—Parts 2-19: Particular requirements for the basic safety and essential performance of infant incubators, Association for the advancement of medical instrumentation, ANSI/AAI/IEC 60601-2-19:2009, pp. 1-19.

Jenkins, S., ScanPod, BabyPod-Products-ScanPod, 2002-2011 Advance Healthcare Technology, ltd., internet website http://babypod.com:80/products/scanpod.php.

Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/2005/1211-inside_the_preemie_brain.htm.

Thermaxx Jackets, 5 most common thermal insulation materials, pp. 1-4, internet: https://www.thermaxxjackets.com/5-most-common-thermal-insulation-materials/.

U.S. Appl. No. 61/994,901, filed May 18, 2014, Rapoport.

Marik et al. "Neonatal incubators: a toxic sound environment for the preterm infant?", Pediatr Crit Care Med, Nov. 2012; Vo. 13(6): pp. 685-689.

International Search Report for PCT application No. PCT/IL2014/050787, dated Dec. 30, 2014.

Ranganna et al. "Reducing noise on the neonatal unit", Infant, vol. 7, Issue 1, pp. 25-28, 2011.

Mahil et al. "Hybrid Swarm Algorithm for the Suppression of Incubator Interference in Premature Infants ECG", Research Journal of Applied Sciences, Engineering and Technology 6(16): 2931-2935, Sep. 10, 2013.

Brown G. "NICU noise and the preterm infant", Neonatal Network, 2009, vol. 28(3): pp. 165-173.

Sang-Hoon Kim. "Air transparent soundproof window", Air Advances, vol. 4, 1171232014.

International Search Report for PCT application No. PCT/IL2014/050786, dated Dec. 30, 2014.

Lichuan Liu et al."Development and applications of active noise control system for infant incubators" Proceedings of the 2009 IEEE International Conference on Systems, Man and Cybernetics, TX, USA, Oct. 2009 pp. 2659-2664.

International Search Report for PCT application No. PCT/IL2014/050785, dated Jun. 8, 2015.

Knutson, A. J. et al "Acceptable noise levels for neonates in the neonatal intensive care unit"., Washington University School of Medicine, 2013.

Japanese Office Action for Application No. JP2016-539684, dated Feb. 25, 2020, 3 pages.

\* cited by examiner

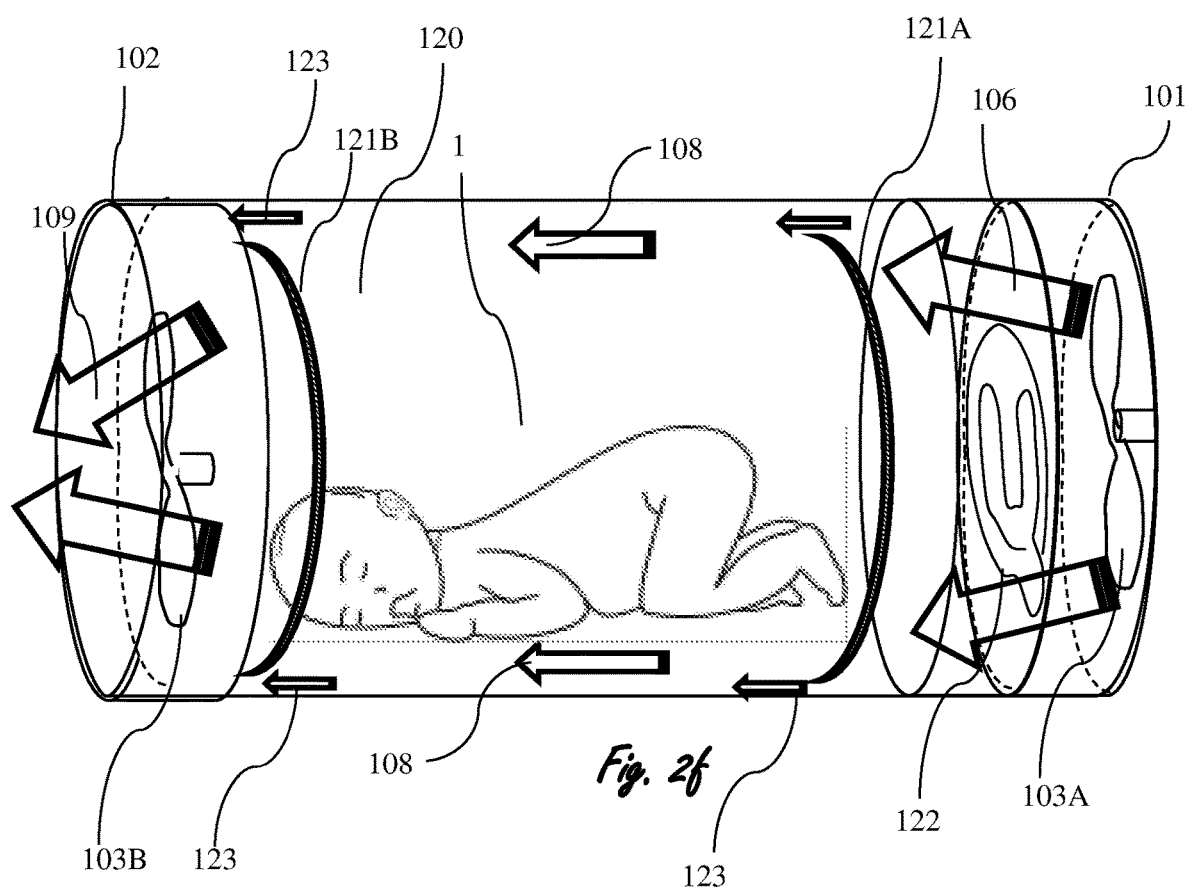

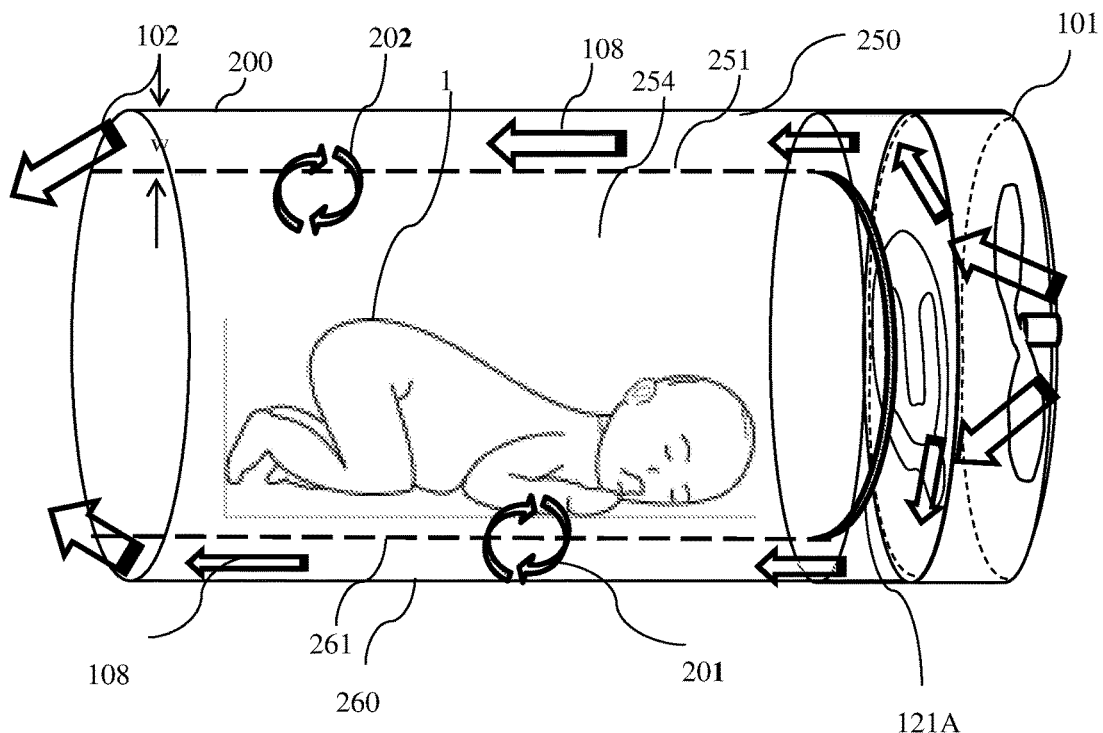
Fig. 3
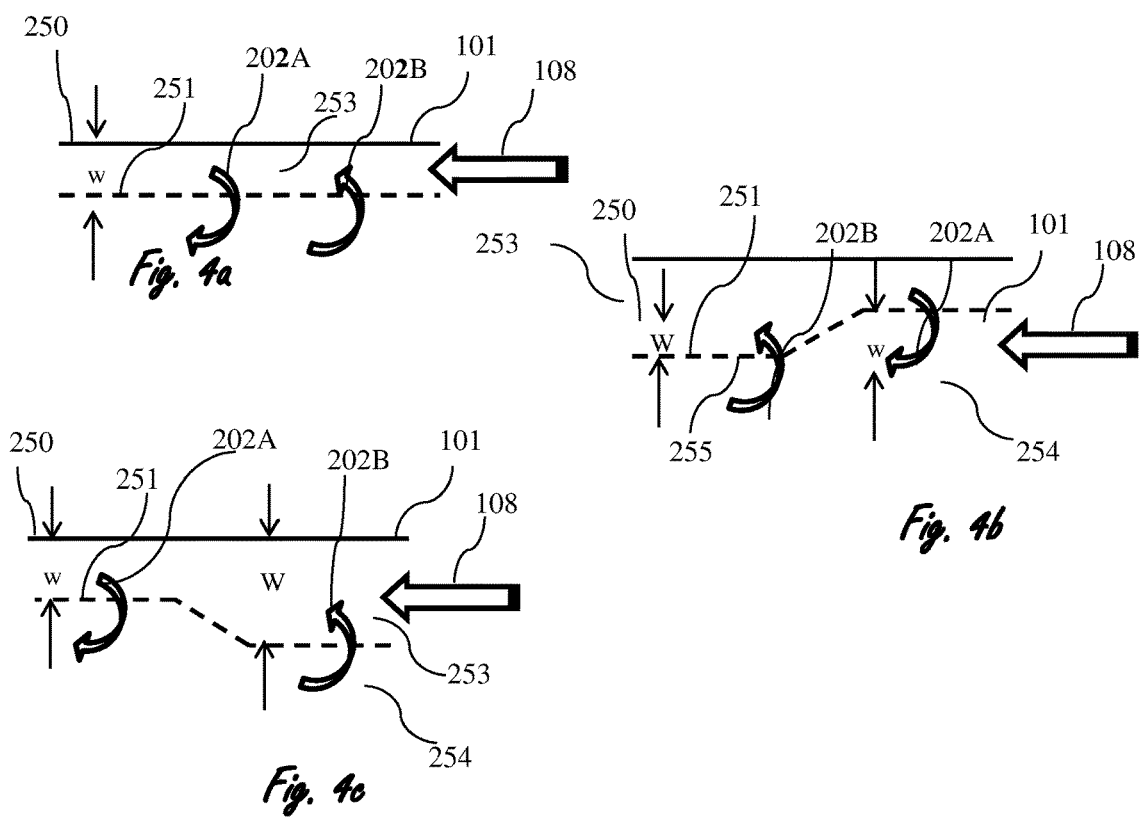
Fig. 4a
Fig. 4b
Fig. 4c

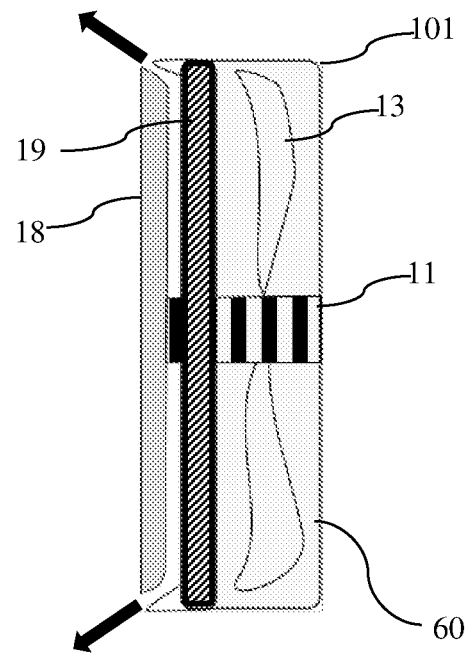
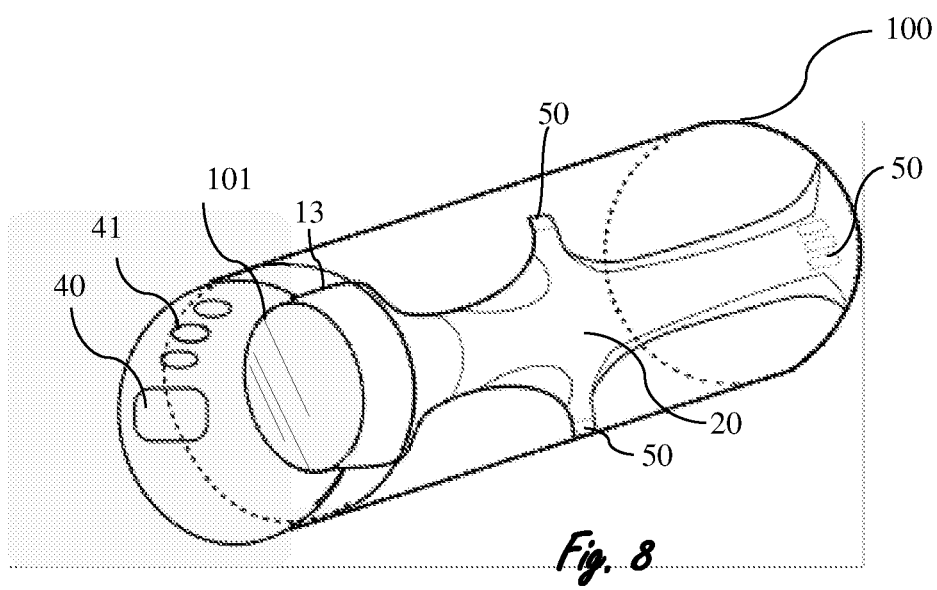

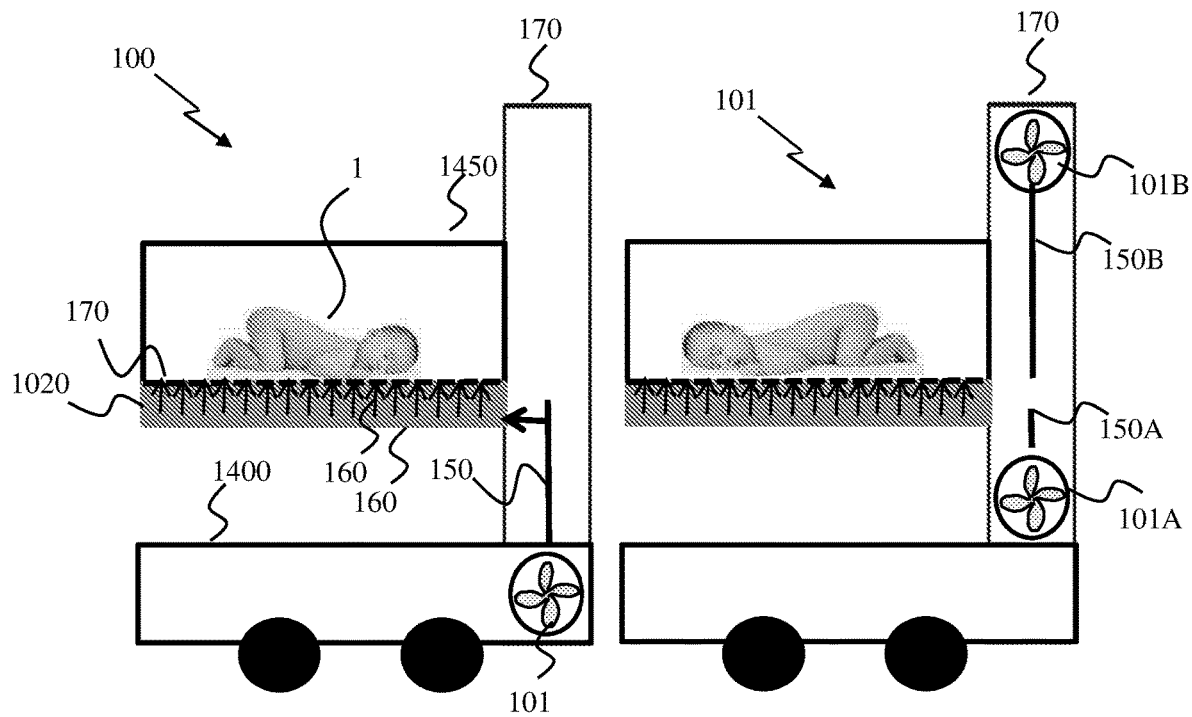
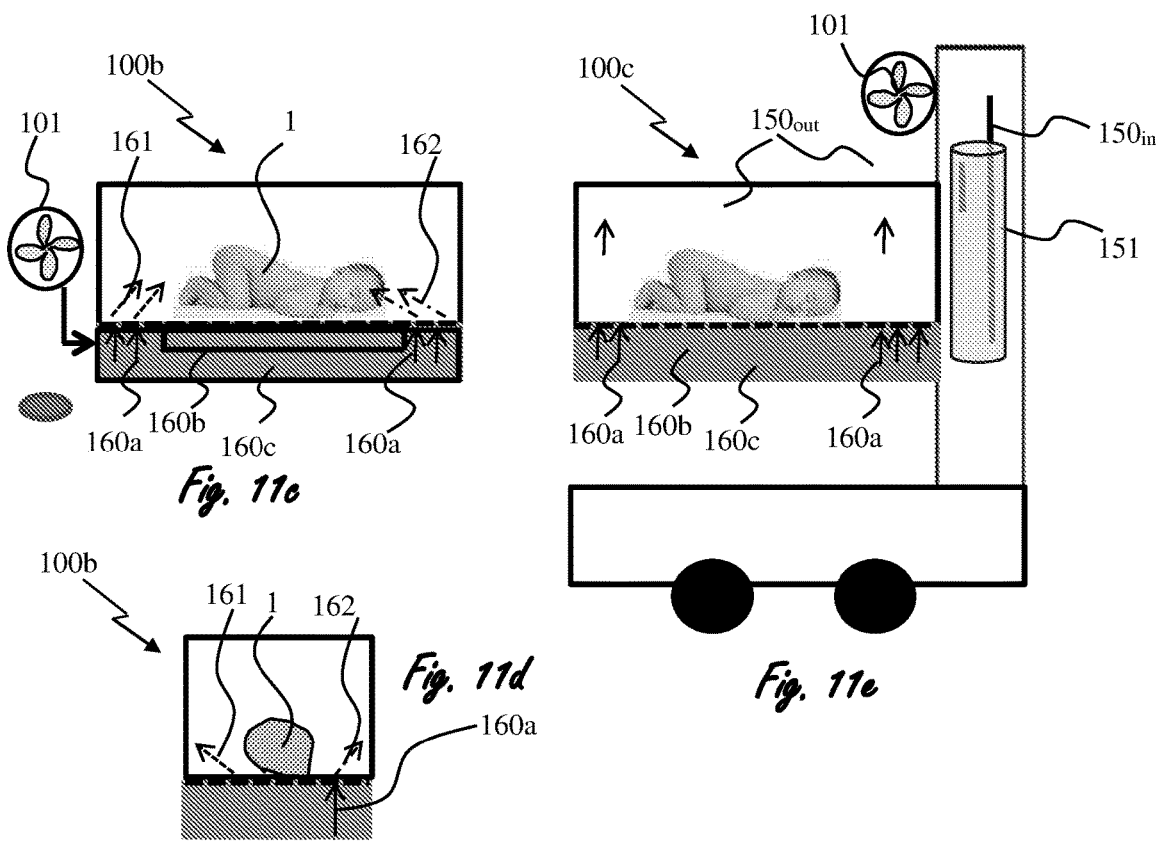

ACTIVE THERMO-REGULATED NEONATAL TRANSPORTABLE INCUBATOR

FIELD OF THE INVENTION

The present invention generally pertains to a vented and thermo-regulated neonate's environment, especially incubators and a thermo regulating system in connection with the same.

BACKGROUND OF THE INVENTION

It was already previously stated that the most common way for regulating the heating of air circulating through an incubator is to control the power delivered to the heater. U.S. RE38453 which is incorporated herein as a reference, discloses an infant incubator, constructed in accordance with the present invention, includes a hood having an access door in a wall thereof and a base upon which the hood is mounted and having a deck which with the hood defines an enclosure. The deck has openings through which air enters and leaves the enclosure. Also included in this incubator is a heater within the base for heating the air and a fan for supplying air to the heater and forwarding the heated air from the heater into the enclosure through at least one of the openings and for returning air from the enclosure to the heater through at least one of the openings. An infant incubator, constructed in accordance with the present invention, further includes sensing means responsive to movement of the access door for sensing when the access door is opened and control means responsive to the sensing means for increasing the heat generated by the heater and increasing the speed of the fan when the access door is opened. Similar technology is disclosed in U.S. Pat. Nos. 6,036,634 and 6,641,521 which are also incorporated herein as references. U.S. Pat. No. 6,511,414 which is also incorporated herein as a reference discloses a neonate's incubator in which thermo-regulated air flows upwardly from air inlet ducts in the base of the incubator, this flow is relatively noisy and can disturb the wellbeing of the neonate.

MRI scanning devices employ magnets to induce a large and stable magnetic field. MRI devices utilize three major types of magnets: Permanent magnets that have a constant magnetic field, super conductive magnets, and resistive magnets. In order to image the patient, the body or body part must be placed in an exact location determined in relevance to the isocenter of the magnetic field.

MRI devices having permanent magnets are known in the art, such as the Aspect M2 ™ platform for MRI devices commercially available from Aspect Magnet Technologies, or another example is as depicted in U.S. Pat. No. 7,719,279 B2, filed 27 May 2008 titled: "SELF-FASTENING CAGE SURROUNDING A MAGNETIC RESONANCE DEVICE AND METHODS THEREOF". The devices usually include two main magnets constructed above and below the table harboring the patient. The exact placing of these top and bottom strong magnets in reference to one another is eminent to reaching the desired magnetic field where the patient is placed.

The thermo regulated neonate's Incubators known in the art, are not suitable for this type of MRI device because the ventilation system placed under the neonate changes the placement of the patient relative to the desired optimal magnetic field, compromising the quality or the received image. It is thus still a long felt need to provide an effective, safe, silent, MRI safe, vented and thermo-regulated neonate's environment, without compromising the patient location in reference to the isocenter of the magnetic field.

SUMMARY OF THE INVENTION

The present invention provides an elongated active thermo-regulated neonatal transportable incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis.

It is another object of the current invention to disclose the ANTI defined in any of the above, wherein at least a portion of the ANTI is configured by means of size and shape to be inserted into an MRD having an open bore in its longitudinal axis; further wherein the ANTI is configured to accommodate the neonate parallel to the MRD bore.

It is another object of the current invention to disclose the ANTI defined in any of the above, wherein at least one of the following holds true: (a) the TRV is a module selected from a group consisting of at least one first venting module, at least one first heating/cooling module, at least one filter located adjacently to either the first venting module or the first heating/cooling module and any combination thereof; (b) the TRV comprises at least one venting module configured to introduce air selected from a group consisting of: heated air, cooled air, humidified air, filtered air, room temperature air, predetermined gas concentrated air, air, and any combination thereof, into the ANTI; (c) the TRV comprises a feedback mechanism for the air quality selected from a group consisting of: temperature, humidity, pressure, airborne particle content, gas concentration, and any combination thereof, configured to maintain the quality in a predetermined value or value range; and, (d) the TRV is a fan, having at least one rotor rotating perpendicularly to a rotor's shaft, and further wherein the shaft is positioned in parallel to the ANTI's main longitudinal axis.

It is another object of the current invention to disclose the ANTI defined in any of the above, additionally comprising air turbulating means (ATM) for slowing and moderating the airflow stream.

It is another object of the current invention to disclose the ANTI defined in any of the above, wherein at least one of the following is held true: (a) the ANTI comprising at least one first TRV located in one of the ends and at least one second TRV located in the opposite end; (b) the at least one TRV is located within the ANTI; (c) the at least one TRV is located outside the ANTI and is in air communication with the ANTI by means of a tubing; and, (d) at least one TRV is in air communication with the ANTI, and at least one TRV is located remotely from the ANTI.

It is another object of the current invention to disclose the ANTI defined in any of the above, wherein the ANTI is in air communication with at least one air recycling mechanism (ARM); the ARM comprising: (a) at least one air inlet for collecting air stream from the ANTI's outer environment; (b) at least one recycled-air outlet for collecting air streamed from the ANTI's inner environment; and (c) at least one air inlet introducing air towards the ANTI's inner environment through the TRV.

It is another object of the current invention to disclose the ANTI defined in any of the above, additionally comprising at least one air flow regulator for regulating at least one air stream selected from a group consisting of: the recycled air stream, the air stream from the ANTI's outer environment, the air streamed towards the ANTI's inner environment, and any combination thereof.

It is another object of the current invention to disclose the ANTI defined in any of the above, having a cross section perpendicular to the main longitudinal axis with a central portion and a peripheral portion, located adjacent to the ANTI's walls; wherein the ANTI further comprising at least one air baffler located at least one position, the position is selected from a group consisting of: the one end, being either proximal or distal, the opposite end, and any combination thereof; the at least one air baffler is positioned within the ANTI at or adjacent to the ANTI's central portion thereby providing between the baffler and the walls apertures for the air to flow along the main longitudinal axis.

It is another object of the current invention to disclose the ANTI defined in any of the above, wherein at least one of the following holds true: (a) the ANTI, the TRV or both comprises at least one air filter; and, (b) the ANTI comprising at least one air channel, configured to direct the airflow within the ANTI.

It is another object of the current invention to disclose the ANTI defined in any of the above, wherein at least one of the following holds true: (a) the ANTI is configured to direct the airflow drift to bypass the location of the neonate residing within; (b) the ANTI is configured to have an air flow of X per volume W and time Y; (c) the ANTI is configured to have an air flow of X per volume W and time Y configurable by the user; auto regulated according to information received by at least one sensor, or both; and, (d) the ANTI is configured to provide linear air flow, turbulent air flow or both within at least a portion of the ANTI inner volume.

It is another object of the current invention to disclose the ANTI defined in any of the above, wherein the ANTI, comprising sound attenuating means configured to at least partially attenuate a selected from a group consisting of: the sounds generated by an MRD, the sound generated by the TRV, the sound of air movement within the ANTI, and any combination thereof.

It is another object of the current invention to disclose the ANTI defined in any of the above, wherein at least one of the following holds true: (a) the ANTI, the TRV or both comprising connections configured to at least partially absorb vibration; and, (b) the ANTI is connected to the TRV by flexible vibration absorptive materials, connectors or both.

It is another object of the current invention to disclose the ANTI defined in any of the above, wherein the ANTI, the TRV or both are connected to externally supplied pressurized gas.

It is another object of the current invention to disclose the ANTI defined in any of the above, wherein at least a portion of the ANTI's walls are double jacket walls arrangement (DJW); the DJW comprising a perforated inner-wall and an intact non-perforated outer-wall, thereby the DJW facilitating the air stream, along the main longitudinal axis in a conduit having a predefined width (w) and length (l).

It is another object of the current invention to disclose the ANTI defined in any of the above, wherein at least one of the following holds true: (a) the width and the length (w, l) are equal along the longitudinal axis, are changed along the longitudinal axis or any combination thereof along the longitudinal axis; and, (b) the conduit between the double jacket walls comprises a selected from a group consisting of: sound attenuating means, thermal isolating materials, vibration reducing means, RF coils, conductive material, non-conductive material, and any combination thereof.

It is another object of the current invention to disclose the ANTI defined in any of the above, wherein at least one portion of the ANTI along the longitudinal axis, the width (W) in ANTI's upper wall is $W_1$ in its proximal side, $W_2$ in its distal side, and in ANTI's lower wall the width is $W_3$ in its proximal side, $W_4$ in its distal side; at least one of the following is held true: (a) $W_1$ is larger than $W_2$ and $W_3$ is larger than $W_4$; (b) $W_1$ is larger than $W_2$ and $W_3$ is smaller than $W_4$; (c) $W_1$ is smaller than $W_2$ and $W_3$ is smaller than $W_4$; (d) $W_1$ is smaller than $W_2$ and $W_3$ is larger than $W_4$; (e) $W_1$ is larger than $W_3$ and $W_2$ is larger than $W_4$; (f) $W_1$ is larger than $W_3$ and $W_2$ is smaller than $W_4$; (g) $W_1$ is smaller than $W_3$ and $W_2$ is smaller than $W_4$; and, (h) $W_1$ is smaller than $W_3$ and $W_2$ is larger than $W_4$.

It is another object of the current invention to disclose the ANTI defined in any of the above, wherein at least a portion of the ANTI, the TRV or both are made of MRI-safe materials.

It is another object of the current invention to disclose the ANTI defined in any of the above, wherein the ANTI comprises a central processing unit (CPU) configured to a selected from a group consisting of: control the TRV, control the TRV by responding to signals received from at least one sensor, control the TRV according to values defined by the user, control the TRV according to predefined physical condition of the neonate, and any combination thereof.

It is another object of the current invention to disclose the ANTI defined in any of the above, wherein at least one of the following holds true: (a) the ANTI comprises at least one aperture configured to be reversibly opened/closed; and, (b) the ANTI is permeable to radiation selected from a group consisting of alpha, beta, gamma, x-ray, magnetic, ionizing, thermal, infrared, sound, and any combination thereof.

It is another object of the current invention to disclose the ANTI defined in any of the above, wherein the ANTI is interconnected to a mobile base by at least one support post, to form a mobile thermo-regulated transportable incubator (MTI).

It is another object of the current invention to disclose the ANTI defined in any of the above, wherein at least one of the following holds true: (a) the mobile base and at least one support are made of MRI safe material; (b) the MTI is configured to be at least partially inserted within an MRD bore; and, (c) the TRV is comprised of at least one venting module located at a selected from a group consisting of: the mobile base, the at least one support, the at least one ANTI end, and any combination thereof; further wherein the venting module is connected to the ANTI by at least one tubing.

The present invention provides a method for thermo-regulating a neonate, characterized by (a) obtaining an elongated, active, thermo-regulated, neonatal transportable incubator (ANTI) having a main longitudinal axis with a proximal end and an opposite distal end; (b) attaching adjacent to one of the ends a temperature regulating vent (TRV); (c) accommodating a neonate in the ANTI in parallel to the main axis; (d) thermo-regulating the ANTI by the TRV; and, (e) streaming air, by means of the TRV, from the end towards the opposite end substantially along the axis;

It is another object of the current invention to disclose the method defined in any of the above, additionally comprising a step of configuring the ANTI by means of size and shape to be at least partially inserted into an MRD having an open bore in its longitudinal axis; further comprising a step of configuring the ANTI to accommodate the neonate, within the bore, parallel to the MRD bore.

The present invention provides a method for imaging neonates by an MRD, comprising the steps of: (a) obtaining an elongated, active, thermo-regulated neonatal transportable incubator (ANTI) having a main longitudinal axis with a proximal end and an opposite distal end comprising in at least one of the ends a temperature regulating vent (TRV), and an MRD comprising an open bore, along the axis; (b) accommodating the neonate in the ANTI, parallel to the axis; (c) thermo regulating the ANTI by the TRV; and, (d) inserting the ANTI into the MRD bore, and imaging, wherein step (c) additionally comprising streaming air by the TRV from the ANTI end towards the opposite end substantially along the axis; further wherein step (d) additionally comprising inserting the ANTI into the MRD bore such that the neonate is parallel to the MRD longitudinal axis.

It is another object of the current invention to disclose the method defined in any of the above, additionally comprising a step of configuring the ANTI by means of size and shape to be at least partially inserted into an MRD having an open bore in its longitudinal axis; further comprising a step of configuring the ANTI to accommodate the neonate, within the bore, parallel to the MRD bore.

The present invention provides a standard of care for thermo-regulating a neonate, comprising steps of: (a) obtaining an elongated active thermo-regulated neonatal transportable incubator (ANTI) having a main longitudinal axis with a proximal end and an opposite distal end; (b) attaching to the at least one of the ends a temperature regulating vent (TRV); (c) accommodating the neonate in the ANTI parallel to the axis; and, (d) thermo-regulating the ANTI by the TRV; wherein the step (d) additionally comprising streaming air by the TRV from the ANTI end towards the opposite end substantially along the axis; further wherein at least one of the following is held true: (a) the noise level in the ANTI is below 60 Decibels; (b) the noise level in the ANTI is below 45 Decibels (c) the temperature in the ANTI is at most 2° C. higher or lower from the set temperature; (d) the $CO_2$ concentration within the ANTI does not exceed 4%; (e) the $O_2$ concentration within the ANTI does not fall below 30 vol. %, and does not exceed 40 vol. %; (f) the air velocity over the mattress within the ANTI does not exceed 0.35 m/s; (g) the amount of thermoregulation related complications of neonates when utilizing the ANTI is b times lower than the average value of thermoregulation complications of neonates; b is equal or greater than 1.05; (h) the average value of salivary cortisol level index from noise derived stress of patient when utilizing the ANTI during MRI is n times lower than the average value during MRI; n is equal or greater than 1.05; (i) the average number of MRI repetition number per patient is p times lower when utilizing the ANTI than the average number of MRI repetitions during MRI of patients; p is equal or greater than 1.05; (j) the average value of salivary cortisol level index from open space related stress of patient when utilizing the ANTI during MRI is q times lower than the average the value during MRI; q is equal or greater than 1.05; (k) the ANTI continues to be used safely in occurrence of a leakage of up to 200 ml deposited in the inner volume of the ANTI; (l) the ANTI remains stable when tilted 10° in normal use and when tilted 20° during transportation; (m) the ANTI does not tip over when encountered with a force of 100 N or less; (n) the average number of patients MRI related fall incidents when utilizing the ANTI is r times lower than the average of patients MRI related fall incidents; r is equal or greater than 1.05; (o) the radiated electromagnetic fields in the inner volume of the ANTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and, (p) the average number of insurable claims of a selected from a group consisting of: manufacturer, handler, user, operator, medical care personal, medical facility, medical facility management or any combination thereof when utilizing the ANTI is v times lower than patient MRI associated insurable claims; v is equal or greater than 1.05.

The present invention provides a thermo-regulating incubator (TRI), comprising: (a) a hood for accommodating a neonate; (b) a base upon which the hood is mounted and through which thermo-regulated air streams towards the same; and, (c) at least one temperature regulating vent (TRV) adapted to stream thermo-regulated air to the base; wherein the TRV is positioned in a location external to the base and the hood.

It is another object of the current invention to disclose the TRI as defined in any of the above, additionally comprising an item selected from a group consisting of a cart, support post, and any combination thereof.

It is another object of the current invention to disclose the TRI as defined in any of the above, wherein the TRV is positioned in a location selected from a group consisting of the cart, the support post, the incubator's top wall, the incubator's side wall and any combination thereof.

It is another object of the current invention to disclose the TRI as defined in any of the above, wherein the TRV comprises at least one opening for introducing air, at least one venting module and at least one heating/cooling system.

It is another object of the current invention to disclose the TRI as defined in any of the above, wherein the TRV additionally comprises an article selected from a group consisting of at least one humidifier, at least one filter, at least one turbulating means and any combination thereof.

It is another object of the current invention to disclose the TRI as defined in any of the above, additionally comprising at least one temperature sensor positioned in a location selected from a group consisting of within the hood, within the base and any combination thereof.

It is another object of the current invention to disclose the TRI as defined in any of the above, wherein the hood comprises at least one opening for inserting the neonate.

It is another object of the current invention to disclose the TRI as defined in any of the above, wherein the hood is mounted to the base through at least one first part of the hood's wall selected from a group consisting of top wall, bottom wall, side wall and any combination thereof.

It is another object of the current invention to disclose the TRI as defined in any of the above, wherein the at least one first part is perforated, thus enabling streaming of thermo-regulated air from within the base to the hood.

It is another object of the current invention to disclose the TRI as defined in any of the above, wherein at least one second part of the hood's wall selected from a group consisting of top wall, bottom wall, side wall and any combination thereof, is perforated; thus enabling streaming of air from within the hood to the environment.

It is another object of the current invention to disclose the TRI as defined in any of the above, additionally comprising at least one first conduit for air-communicating the TRV to the base.

It is another object of the current invention to disclose the TRI as defined in any of the above, additionally comprising least one second conduit for air-communicating the base to the hood.

The present invention provides a method for thermo-regulating an incubator's hood, comprising steps of (a) providing an incubator comprising a hood and a base upon which the hood is mounted; (b) air communicating at least one temperature regulating vent (TRV) with the base; and, (c) temperature regulating air within the hood by the TRV whilst streaming thermo-regulated air from the TRV, via the base, towards the hood; wherein the method additionally comprising a step of positioning the TRV in a location external to the hood and the base.

It is another object of the current invention to disclose the method as defined in any of the above, additionally comprising step of attaching the incubator to an item selected from a group consisting of the cart, the support post, and any combination thereof.

It is another object of the current invention to disclose the method as defined in any of the above, additionally comprising step of positioning the TRV in a location selected from a group consisting of the cart, the support post, the incubator's top wall, the incubator's side wall and any combination thereof.

It is another object of the current invention to disclose the method as defined in any of the above, additionally comprising steps of: (a) introducing air to the TRV through at least one opening; (b) pushing the air through at least one venting module; and, (c) thermo-regulating the air through at least one heating/cooling system.

It is another object of the current invention to disclose the method as defined in any of the above, additionally comprising a step of humidifying the air.

It is another object of the current invention to disclose the method as defined in any of the above, additionally comprising a step of filtering the air.

It is another object of the current invention to disclose the method as defined in any of the above, additionally comprising a step of turbulating the air.

It is another object of the current invention to disclose the method as defined in any of the above, additionally comprising a step of attaching at least one temperature sensor at a location selected from within the hood, within the base and any combination thereof.

It is another object of the current invention to disclose the method as defined in any of the above, additionally comprising a step of inserting the neonate through at least one opening in the hood.

It is another object of the current invention to disclose the method as defined in any of the above, additionally comprising a step of mounting the base to at least one first part of the hood's wall selected from a group consisting of top wall, bottom wall, side wall and any combination thereof.

It is another object of the current invention to disclose the method as defined in any of the above, additionally comprising a step of perforating the at least one first part, thus enabling streaming of thermo-regulated air from within the base to the hood.

It is another object of the current invention to disclose the method as defined in any of the above, additionally comprising a step of perforating at least one second part of the hood's wall selected from a group consisting of top wall, bottom wall, side wall and any combination thereof, thus enabling streaming of air from within the hood to the environment.

It is another object of the current invention to disclose the method as defined in any of the above, additionally comprising a step of air-communicating the TRV to the base by at least one first conduit.

It is another object of the current invention to disclose the method as defined in any of the above, additionally comprising a step of air-communicating the base to the hood by at least one second conduit.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing: In order to understand the invention and to see how it may be implemented in practice, a few preferred embodiments will now be described, by way of non-limiting example only, with reference to be accompanying drawings, in which:

FIG. 2f, illustrating in a non-in-scale manner a partially perspective side view of the ANTI (120) comprising at least one baffle;

FIG. 3, illustrating in a non-in-scale manner a partially perspective side view of an ANTI comprising double jacket walls (200);

FIG. 4a, schematically illustrating a cross-section of a portion of the upper (infant's ceiling side) double jacket of the walls (250, 251), width (w) is equal along the conduit (253) providing air inflow and outflow (202B, 202A);

FIG. 4b, schematically illustrating a cross-section of a portion of the upper (infant's ceiling side) double jacket of the walls (250, 251) of an ANTI in non-limiting and out-of-scale manners; Width is varied in a manner that initial width (w) is narrow and then width increases (W);

FIG. 4c, schematically illustrating a cross-section of a portion of the upper (infant's ceiling side) the double jacket of the walls of an ANTI (250, 251) in non-limiting and out-of-scale manners; Here again, thermo-regulated air flow (108) is streamed from the proximal side of the incubator (101) via conduit (253); Width is varied in a manner that initial width (W) decrease along the conduit to a width w;

FIG. 7, schematically illustrating a side view of an embodiment of a TRV;

FIG. 8, schematically illustrating a perspective view of an ANTI for accommodating a neonate ventilated and/or thermo-regulated by a TRV comprising a side channel;

FIG. 11A illustrating in a non-in-scale manner one embodiment of the current invention in which the TRV is positioned on the incubator's cart (100);

FIG. 11B illustrating in a non-in-scale manner one embodiment of the current invention in which the TRV is positioned on the incubator's support (100);

FIG. 11C illustrating in a non-in-scale manner one embodiment of the current invention in which the TRV is positioned on the incubator's side wall (100);

FIG. 11D illustrating in a non-in-scale manner one embodiment of the current invention in which the TRV is positioned on the incubator's top wall (100);

FIG. 11E illustrating in an out of scale manner a face view cross-section an embodiment of an incubator (102);

DETAILED DESCRIPTION OF THE PREFERRED EMBODIMENTS

Figures 1A, 1B:
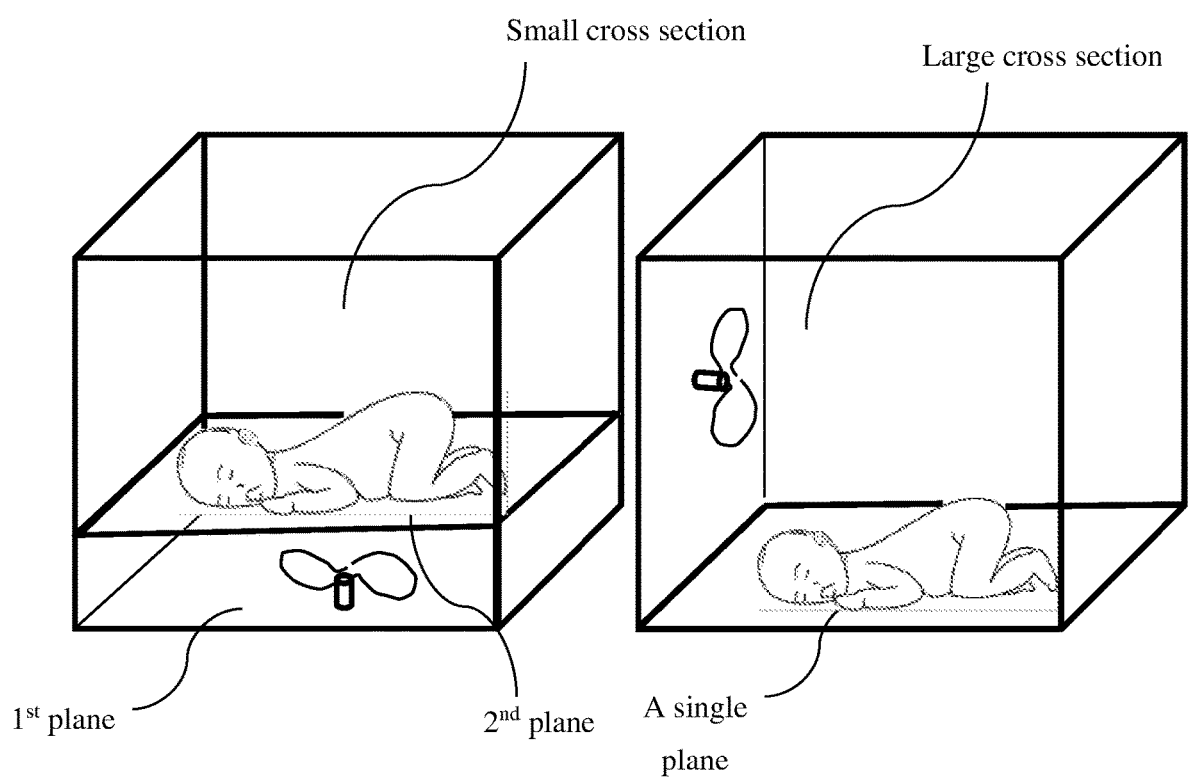
FIG. 1a, illustrating in a non-in-scale manner an example of prior art of an active neonates transportable incubator (ANTI) with an TRV located at its bottom.
FIG. 1b, illustrating in a non-in-scale manner one embodiment of the current invention in which a TRV is located at the proximal end of an ANTI.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured.

The essence of the present invention is to provide a thermo-regulating neonatal transportable incubator. Thermo-regulation is carried out by a temperature regulating mechanism, such as a thermo regulating vent (TRV) located at the end of an elongated container of the incubator. The TRV introduces thermo-regulated air to the container in a quiet and gentle flow parallel to the longitudinal axis of the container.

The invention pertains to an active neonatal transportable incubator (ANTI) which is MRI-safe.

The invention additionally pertains to an incubator with a temperature regulating vent located outside the incubator and its base.

The term "neonate's accommodating means" refers hereinafter to any means useful for holding a neonate in a position within an incubator in parallel to its longitudinal axis. This position can be in lying, substantially horizontal, position (on his/hers back, stomach, or side), in an at least partially reclining position, or in at least partially sitting position.

The term "thermo-regulated environment" or "thermo-regulated neonate's environment" refers hereinafter to an environment that its air temperature is in a constant predetermined temperature with an error of $\pm 2°$ C.

The term "along" refers hereinafter to a parallel flow, to a rotational coil-like flow or any combination thereof.

The term "venting module" refers hereinafter to a module that circulates air and distributes it either evenly or in a defined direction. More specifically the term relates to a fan, a jet, a blower, a compressor, a pump, air streamer, propeller, ventilator, thermantidote, axial-flow fans, centrifugal fan, cross-flow fan, airflow generated using the Coandă effect, etc.

The term "temperature regulating vent (TRV)" refers hereinafter to a system that regulates the temperature of air and streams it to its destination. The TRV include a heating/cooling system and a venting module. It may also contain air turbulating means, humidifier and filters.

The term "heating/cooling module" refers hereinafter to a module that controls the temperature either by heating or by cooling or by doing both. More specifically the term relates to an air conditioned system, an infrared heater, a water/oil-heated radiator, a coiled heater, an open coil air heater, a round open coil air heater, a convection heater, straight or formed tubular heaters, a quartz tube air heater, a capacitor-type heater, a Pelletier module, etc.

The term "baffle" refers hereinafter to a low-directing or obstructing vanes or panels. More specifically the term relates to longitudinal flow baffles, impingement baffles, orifice baffles, single segmental baffles, double segmental, etc.

The term "turbulent flow" refers herein after to the motion of a fluid having local velocities and pressures that fluctuate randomly. The movement of the fluid (e.g. liquid, gas) in characterized by having subcurrents displaying turbulence, moving in irregular patterns, while the overall flow is in one direction. In turbulent flow the speed of the fluid at a point is continuously undergoing changes in both magnitude and direction.

The term "linear flow" refers herein after to laminar flow of a liquids or gases (e.g. air) in a laminar flow, in which the fluid moves in smooth paths or layers. Flow in which turbulence is not exhibited is called laminar.

The term "air turbulating means" refers hereinafter to any means that controls, softens, moderates and gentles air-stream. More specifically the term relates to pre active members, such as fan, multiple-fan arrangement or cascade thereof, air pump, Dyson-type bladeless air multiplier, venting apparatus etc., and/or passive members, such as texturized strainer, curved conduits in a continuous barrier etc.

The term "air humidifying means" refers hereinafter to any appliance that increases humidity (moisture) of air.

The term "Venturi effect" refers hereinafter to the reduction in fluid or gas pressure that results when a fluid flows through a constricted section of pipe. The velocity of the fluid or gas increases as the cross sectional area decreases, with the static pressure correspondingly decreasing.

The term "air communication" refers hereinafter to a communication between two objects that allow flow of air at least one direction between them.

The term "fluid communication" refers hereinafter to a communication between two objects that allow flow of matter (gas, fluid or solid) at least one direction between them, the term includes ant form of air communication.

The term "proximal side" refers hereinafter to the side of the longitudinal axis in which a TRV is embedded.

The term "distal side" refers hereinafter to the side of the longitudinal axis opposite to the proximal side in which a TRV is embedded.

The term "sound shield" refers herein after to any barriers or sound reflection panel, screens, baffle, single or a plurality of, configured to lowering the sound reaching the neonate.

According to another embodiment of the present invention the ANTI further comprises at least one sound shield configured to at least partially insulate the neonate from the sound external to the incubator.

The term "neonate" interchangeably refers herein after to a term selected from a group of: neonate, newborn, baby, infant, toddler, child, adolescent, adult, elderly, patient, individual, subject, inmate, sufferer, outpatient, case, client, etc.; further this term refers to person, animal, or sample, as a whole or a portion thereof.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further in some embodiments at least a portion of this material is imbedded with non-transparent materials for means of strength and/or conductivity such as metallic wires.

The term "sensor" interchangeably refers hereinafter to any device that receives a signal or stimulus (heat, pressure, light, motion, sound, humidity etc.) and responds to it in a distinctive manner. This manner can be such as inducing the action/inaction of other devices, inducing the action/inaction of indicators (visual, auditable or sensible), inducing the display of the input received by the sensor, inducing the data storage/analysis of input in a central processing unit, etc.

The term "life supporting equipment" interchangeably refers hereinafter to any element that provides an environmental condition, a medical condition or monitoring of an environmental or medical condition thereof that assists in sustaining the life of a neonate and/or bettering their physical and physiological wellbeing. This element can be: (a) any medical equipment: all devices, tubes, connectors, wires, liquid carriers, needles, sensors, monitors, etc., that are used by medical personal in association with the patient. This equipment is such as bilirubin light, an IV (intravenous) pump, oxygen supplementation systems by head hood or nasal cannula, continuous positive airway pressure system, a feeding tube, an umbilical artery catheter, a fluid transport device, hemofiltration system, hemodialysis system, MRI contras solution injection, imaging the neonate etc.; (b) medical measurement and observation systems (including sensors and/or monitors) of temperature, respiration, cardiac function, oxygenation, brain activity such as ECG (electrocardiography) monitor, blood pressure monitor, cardio-respiratory monitor, pulse oximeter; and (c) environmental control systems such as ventilator, air conditioner, humidifier, temperature regulator, climate control systems, noise muffling device, vibration muffling device, etc. and any combination thereof.

The term "medical equipment tubing" interchangeably refers hereinafter to all tubes, cables, connectors, wires, liquid carriers, gas carriers, electrical wires, monitoring cables, viewing cables, data cables, etc., that is used in connection to life support equipment, medical equipment or physical environment maintenance or monitoring.

The term "CPU", central processing unit, interchangeably refers hereinafter to the hardware within a computer that carries out the instructions of a computer program by performing the basic arithmetical, logical, and input/output operations of the system. In the embodiments of the invention the CPU can be connected to: a user interface, at least one sensor, at least one indicator, at least one venting module, at least one temperature regulating vent, at least one air filter, at least one sound filter, at least one humidifier, at least one air circulating mechanism, life supporting equipment, a control panel, a monitoring device, a viewing or filming device, and etc., at last one engine configured to convert electrical power into movement of such as a vent, a baffle, a recline-able neonate restraint means, sealing of at least one opening in the incubator, or and etc., thus providing the user monitoring and/or control over various aspects of the invention.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR), any Laser magnetic resonance device, any Quantum Rotational field magnetic resonance device (cyclotron), and any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device. Additionally or alternatively, the MRD is self-fastening cage surrounding a magnetic resonance device as depicted in U.S. Pat. No. 7,719,279 B2, filed 27 May 2008 titled: "SELF-FASTENING CAGE SURROUNDING A MAGNETIC RESONANCE DEVICE AND METHODS THEREOF", of which is hereby incorporated by reference in its entirety.

The term "MRI-safe" interchangeably refers herein to any material that, when used in the MR environment, will present no additional risk to the patient and not significantly affect the quality of the diagnostic information. The material is completely non-magnetic, non-electrically conductive, and non-RF reactive, eliminating all of the primary potential threats during an MRI procedure.

The term "sound attenuation means" interchangeably refers herein to any means configured for attenuating or muffling general and specific sounds, including:

passive acoustic attenuators such as resonators designed for specific frequencies, sound absorptive materials and linings. Passive sound absorptive materials that are used incorporated with the ANTI and/or TRV, having at least a portion of the sound energy dissipated within the medium itself as sound travels through them can be such as porous materials commonly formed of matted or spun fibers; panel (membrane) absorbers having an impervious surface mounted over an airspace; and resonators created by holes or slots connected to an enclosed volume of trapped air. Common porous absorbers allow air to flow into a cellular structure where sound energy is converted to heat. These may include a thick layer of cloth or carpet, spray-applied cellulose, aerated plaster, fibrous mineral wool and glass fiber, open-cell foam, and felted or cast porous ceiling tile. Thickness plays an important role in sound absorption by porous materials.

Other absorbers are panel absorbers. Typically, panel absorbers are non-rigid, non-porous materials which are placed over an airspace that vibrates in a flexural mode in response to sound pressure exerted by adjacent air molecules for example thin wood paneling over framing, lightweight impervious ceilings and floors, glazing and other large surfaces capable of resonating in response to sound.

The term "resonators" interchangeably refers herein to a structure configured to typically act to absorb sound in a narrow frequency range. Resonators include some perforated materials and materials that have openings (holes and slots). Such as a Helmholtz resonator, which has the shape of a bottle. The resonant frequency is governed by the size of the opening, the length of the neck and the volume of air trapped in the chamber. Typically, perforated materials only absorb the mid-frequency range unless special care is taken in designing the facing to be as acoustically transparent as possible.

active sound controlling devices that create destructive interferences using a secondary source of noise such as using actuator loudspeakers. Some active sound controlling devices use active feedback mechanisms utilizing information received from sound sensors in various locations, and respond to the specific frequency and sound level received. An active sound control mechanism can be efficiently employed in a system with a vent whose generated sound frequency can be calculated.

hybrid sound attenuating systems that employ both active and passive elements to achieve sound reduction and adaptive-passive systems that use passive devices whose parameters can be varied in order to achieve optimal noise attenuation over a band of operating frequencies, such as a tunable Helmholtz resonator.

The term "patient table" in reference to a magnetic resonance device interchangeably refers herein to such as a countertop, shelf, stretcher, bed, cradle, restraining device, recliner, chair, or any object designated for placing the patient while being imaged. In magnetic resonance devices, the location of the patient bed is carefully determined as to be placed optimally in reference to the magnetic field generated by the magnets.

The term "air filter" interchangeably refers herein to any a device configured to remove solid particulates from the air. Typically the filter removes particles of fibrous materials such as dust, pollen, mold, and bacteria from the air, excess humidity, smoke particles, allergens, pet dander, mold spores, dust mite feces, bacteria, viruses, any molecule derived from bacteria, viruses protozoa, animal; any predetermined airborne molecular contaminates such as volatile organic compounds or ozone, etc., and any combination thereof. The filter is such as a chemical filter, air ionisers, oil bath filters air purifier, HEPA filter, and etc. the filter can further employ an air purifying mechanism known in the art, such as passing an electrical current, or static, thermodynamic sterilization system, ultraviolet germicidal irradiation, activated carbon, photocatalytic oxidation electrostatic precipitators, titanium dioxide ($TiO_2$) technology, and etc.

The term "emergency shut-down mechanism" interchangeably refers herein to any mechanism configured to stop the operation of at least one of the following: TRV, ventilation module, heating/cooling module, air recycling system, active sound attenuating means, active air filters (such as ionisers, thermodynamic, electrostatic, UV generating, and etc.), feedback mechanism, CPU, air turbulating mechanism, immediately. Typically this is done by a single step of the user, like for example pulling/pushing a lever or a button. Further this can include opening of the ANTI.

The term "base" in reference to the incubator, refers hereinafter to the foundation of the incubator that provides support to the hood. The base attached to the hood through its upper wall, bottom wall or any of the side walls. The base can also be attached to only part of the wall. The base is supposed to also transfer thermo-regulated air from the TRV to the interior of the hood.

The term "cart" refers hereinafter to any apparatus used for transporting the cart. This includes any transport device or any small vehicle pushed or pulled by manually, automatically or both. More specifically the term relates to a structure able to hold the incubator having mobility providing elements such as one or a plurality of a wheel, roller, sliding blade, rotating belt, etc. For example, trolley, handcart, pushcart, electric cart, wagon, barrow, rickshaw, ruck, wagon, barrow, buggy, dolly, carriage, float, cab, dray, gig, gurney, handcart, palanquin, pushcart, tumbrel, wheelbarrow, curricle, etc.

The term "incubator" interchangeably refers hereinafter to a special unit specializing in the care of ill or premature newborn infants. This includes a stationary incubator, a moveable incubator, a transport incubator, a disposable incubator, a healthcare facility incubator, portable incubator, an intensive care incubator, an incubator intended for home use, an incubator for imaging a neonate, a treatment incubator, a modular incubator, an isolating incubator and any combination thereof. The neonatal incubator is a box-like enclosure in which an infant can be kept in a controlled environment for observation and care. The incubator usually includes observation means to the accommodated neonate, and openings for the passage of life support equipment, and the handler's hands. At least partially enclosed environment formed within the incubator is at least partially isolated from the external environment conditions such as noise, vibration, drift, temperature, light, gas concentrations, humidity, microorganisms, etc., and/or regulated to reach life supporting parameters defined by medical personal. The incubator can contain, or be connected to life supporting equipment. The internal environment can be controlled by environment control systems such as temperature regulating, ventilating, humidifying, lighting, moving, noise reduction systems, vibration reducing systems, etc.

The term "support post" or "support pillar" refers hereinafter to a post supporting or holding the incubator. The post may hold additional devices connected to the incubator.

According to one embodiment of the invention An elongated active thermo-regulated neonatal transportable incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis.

It is still in the scope of the present invention to provide the ANTI as described above, wherein the ANTI is configured by means of size and shape to be inserted into an MRD having an open bore in its longitudinal axis; further wherein the ANTI is configured to accommodate the neonate, parallel to the MRD bore. It is within the scope of the invention wherein the ANTI is configured to accommodate the neonate in proximity to an MRD patient table, or any predefined location relative to the magnetic isocenter of the main magnets providing the homogenous magnetic field. Preferably locating the neonate as adjacent as possible to the isocenter of an existing magnetic resonance imaging device. As a non-limiting example this is achieved by having the bottom part of the transportable incubator as thin as possible thus limiting the distance of the neonate form the originally designed patient location.

Additionally or alternatively, the ANTI comprises adjustment means configured to maneuver the location of the neonate within the ANTI such that the neonate is placed optimally relative to the main magnetic field isocenter.

Additionally or alternatively, the ANTI comprises additional RF coils adjacent to the neonate, in order to improve the imaging process.

According to another embodiment of the invention, an ANTI as defined above is disclosed, wherein the TRV is a module selected from a group consisting of at least one first venting module, at least one first heating/cooling module, at least one filter located adjacently to either the first venting module or the first heating/cooling module and any combination thereof.

According to another embodiment of the invention, an ANTI as defined above is disclosed, wherein the TRV is a module comprising at least one venting module configured to introduce air selected from a group consisting of: heated air, cooled air room temperature air and any combination thereof into the ANTI. Additionally or alternatively, the TRV comprises at least one first vent configured to stream air from the outside and at least one second vent configured to stream air originating at the air streamed by at least one first vent.

According to another embodiment of the invention, an ANTI as defined above is disclosed, wherein the TRV comprises a feedback mechanism for the air quality selected from a group consisting of: temperature, humidity, airborne particle content, gas concentration, and any combination thereof, configured to maintain the quality in a predetermined value or value range.

According to another embodiment of the invention, an ANTI as defined above is disclosed, wherein the TRV is a fan, having at least one rotor rotating perpendicularly to a rotor's shaft, and further wherein the shaft is positioned in parallel to the ANTI's main longitudinal axis.

According to another embodiment of the invention, an ANTI as defined above is disclosed, additionally comprising air turbulating means (ATM) for slowing and moderating the airflow stream, the ATM is located adjacently to the TRV.

Additionally or alternatively, the ATM is located in a selected from a group consisting of: within the inner volume of the ANTI, within air tubing connected to at least a portion of the ANTI, connected to the TRV, and any combination thereof.

According to another embodiment of the invention, an ANTI as defined above is disclosed, wherein at least one of the following is held true: (a) the ANTI comprising at least one first TRV located in one of the ends and at least one second TRV located in the opposite end; (b) at least one TRV is located within the ANTI; (c) at least one TRV is located outside the ANTI and is in air communication with the ANTI by means of a tubing; (d) at least one TRV is in air communication with the ANTI, and at least one TRV is located within ANTI's support (1520); (e) at least one TRV is in air communication with the ANTI, and at least one TRV is located within ANTI's canopy (1560); (f) at least one TRV is in air communication with the ANTI, and at least one TRV is located within ANTI's trolley (1501); and, (g) at least one TRV is in air communication with the ANTI, and at least one TRV is located remotely from the ANTI.

According to another embodiment of the invention, an ANTI as defined above is disclosed, wherein the ANTI is in air communication with at least one air recycling mechanism (ARM); the ARM comprising: (a) at least one air inlet for collecting air stream from the ANTI's outer environment; (b) at least one recycled-air inlet for collecting air streamed from the ANTI's inner environment; and, (c) at least one air outlet introducing air towards the ANTI's inner environment through the TRV.

According to another embodiment of the invention, an ANTI as defined above is disclosed, additionally comprising at least one air flow regulator for regulating at least one air stream selected from a group consisting of: the recycled air stream, the air stream from the ANTI's outer environment, the air streamed towards the ANTI's inner environment, and any combination thereof.

According to another embodiment of the invention, an ANTI as defined above is disclosed, having a cross section perpendicular to the main longitudinal axis with a central portion and a peripheral portion, located adjacent to the ANTI's walls; wherein the ANTI further comprising at least one air baffler located at least one position, the position is selected from a group consisting of: one end, being either proximal or distal, the opposite end, and any combination thereof; at least one air baffler is positioned within the ANTI at or adjacent to the ANTI's central portion thereby providing between the baffler and the walls apertures for the air to flow along the main longitudinal axis.

According to another embodiment of the invention, an ANTI as defined above is disclosed, wherein the ANTI, the TRV or both comprises at least one air filter.

According to another embodiment of the invention, an ANTI as defined above is disclosed, wherein the ANTI is configured to direct the airflow drift to bypass the location of the neonate residing within.

According to another embodiment of the invention, an ANTI as defined above is disclosed, wherein the ANTI comprising at least one air channel, configured to direct the airflow within the ANTI.

According to another embodiment of the invention, an ANTI as defined above is disclosed, wherein the ANTI is configured to have an air flow of X per volume W and time Y.

According to another embodiment of the invention, an ANTI as defined above is disclosed, wherein the air flow parameters of X, W, and Y are configurable by the user.

According to another embodiment of the invention, an ANTI as defined above is disclosed, wherein the air flow parameters of X, W, and Y are automatically adjusted by means of at least one CPU configured to control the TRV according to information received by at least one sensor.

According to another embodiment of the invention, an ANTI as defined above is disclosed, wherein the ANTI, TRV or both comprising sound attenuating means configured to at least partially muffle the sound of the TRV and air movement within the ANTI.

According to another embodiment of the invention, an ANTI as defined above is disclosed, wherein the ANTI, comprising sound attenuating means configured to muffle the sounds generated by the MRD.

According to another embodiment of the invention, an ANTI as defined above is disclosed, wherein the ANTI comprises at least one resonator configured to reflect the sound waves so as to cancel out frequencies generated by the air flow and/or vent.

According to another embodiment of the invention, an ANTI as defined above is disclosed, wherein the ANTI, the TRV or both comprising connections configured to at least partially absorb vibration.

According to another embodiment of the invention, an ANTI as defined above is disclosed, wherein the ANTI is connected to the TRV by flexible vibration absorptive materials, connectors or both.

According to another embodiment of the invention, an ANTI as defined above is disclosed, wherein the ANTI, the TRV or both are connected to externally supplied pressurized gas.

According to another embodiment of the invention, an ANTI as defined above is disclosed, wherein at least a portion of the ANTI's walls are double jacket walls arrangement (DJW); the DJW comprising a perforated inner-wall and an intact non-perforated outer-wall, thereby the DJW facilitating the air stream, along the main longitudinal axis in a conduit having a predefined width (w) and length (l).

According to another embodiment of the invention, an ANTI as defined above is disclosed, wherein the width and the length (w, l) are equal along the longitudinal axis.

According to another embodiment of the invention, an ANTI as defined above is disclosed, wherein the width or the length (w, l) changes along the longitudinal axis.

According to another embodiment of the invention, an ANTI as defined above is disclosed, wherein in at least one portion of the ANTI along the longitudinal axis, the width (W) in ANTI's upper wall is $W_1$ in its proximal side, $W_2$ in its distal side, and in ANTI's lower wall the width is $W_3$ in its proximal side, $W_4$ in its distal side; at least one of the following is held true: (a) $W_1$ is larger than $W_2$ and $W_3$ is larger than $W_4$; (b) $W_1$ is larger than $W_2$ and $W_3$ is smaller than $W_4$; (c) $W_1$ is smaller than $W_2$ and $W_3$ is smaller than $W_4$; (d) $W_1$ is smaller than $W_2$ and $W_3$ is larger than $W_4$; (e) $W_1$ is larger than $W_3$ and $W_2$ is larger than $W_4$; (f) $W_1$ is larger than $W_3$ and $W_2$ is smaller than $W_4$; (g) $W_1$ is smaller than $W_3$ and $W_2$ is smaller than $W_4$; and, (h) $W_1$ is smaller than $W_3$ and $W_2$ is larger than $W_4$.

According to another embodiment of the invention, an ANTI as defined above is disclosed, wherein at least a portion of the ANTI, the TRV or both are made of MRI-safe materials.

According to another embodiment of the invention, an ANTI as defined above is disclosed, wherein at least a portion of the ANTI comprises materials selected from a group consisting of: vibration absorptive, sound absorptive, liquid resistant, fire resistant, recyclable materials, disposable materials, and any combination thereof.

According to another embodiment of the invention, an ANTI as defined above is disclosed, wherein the ANTI comprises at least one sensor selected from a group consisting of: a temperature sensor, a motion sensor, a breathing sensor, a gas concentration sensor, an air low sensor, a humidity sensor, a door opening or closing sensor, a weight sensor, an RF sensor, and any combination thereof.

According to another embodiment of the invention, an ANTI as defined above is disclosed, wherein the sensors are configured to relay sensed information to a CPU, an indicator, or both.

According to another embodiment of the invention, an ANTI as defined above is disclosed, wherein the ANTI comprises a central processing unit (CPU).

According to another embodiment of the invention, an ANTI as defined above is disclosed, wherein the CPU is configured to a selected from a group consisting of: control the vent, control the vent by responding to signals received from at least one sensor, control the vent according to values defined by the user, control the vent according to predefined physical condition of the neonate, and any combination thereof.

According to another embodiment of the invention, an ANTI as defined above is disclosed, wherein the TRV comprises an emergency shut-down mechanism.

According to another embodiment of the invention, an ANTI as defined above is disclosed, wherein the ANTI is connected to life supporting equipment.

According to another embodiment of the invention, an ANTI as defined above is disclosed, wherein the ANTI comprises at least one aperture configured to be reversibly opened/closed.

According to another embodiment of the invention, an ANTI as defined above is disclosed, wherein the ANTI is interconnected to a mobile base by at least one support, to form a mobile thermo-regulated transportable incubator (MTI).

According to another embodiment of the invention, an ANTI as defined above is disclosed, wherein the mobile base and at least one support are made of MRI safe material.

According to another embodiment of the invention, an ANTI as defined above is disclosed, wherein the MTI is configured to be at least partially inserted within an MRD bore.

According to another embodiment of the invention, an ANTI as defined above is disclosed, wherein the ANTI comprises at least one port configured for the docking or passage of life support equipment, tubing or both.

According to another embodiment of the invention, an ANTI as defined above is disclosed, wherein the ANTI comprises at least one port configured for the docking or passage of life support equipment, tubing or both.

According to another embodiment of the invention, an ANTI as defined above is disclosed, wherein the TRV is comprised of at least one venting module located at a selected from a group consisting of: the mobile base, at least one support, at least one ANTI end, and any combination thereof; further wherein the venting module is connected to the ANTI by at least one tubing.

According to another embodiment of the invention, a method for thermo-regulating a neonate, characterized by (a) obtaining an elongated, active, thermo-regulated, neonatal transportable incubator (ANTI) having a main longitudinal axis with a proximal end and an opposite distal end; (b) attaching adjacent to one of the ends a temperature regulating vent (TRV); (c) accommodating a neonate in the ANTI in parallel to the main axis; (d) thermo-regulating the ANTI by the TRV; and, (e) streaming air, by means of the TRV, from the end towards the opposite end substantially along the axis.

According to another embodiment of the invention, a method as defined above is disclosed, additionally comprising a step of configuring the ANTI by means of size and shape to be inserted into an MRD having an open bore in its longitudinal axis, and a patient table within the open bore; further comprising a step of configuring the ANTI to: (a) accommodate the neonate, within the bore, parallel to the MRD bore; and, (b) accommodate the neonate in proximity to the MRD patient table.

According to another embodiment of the invention, a method as defined above is disclosed, additionally comprising a step of selecting the TRV from a group of modules consisting of at least one first venting module, at least one first heating/cooling module, at least one filter located adjacently to either the first venting module or the first heating/cooling module and any combination thereof.

According to another embodiment of the invention, a method as defined above is disclosed, additionally comprising a step of selecting the TRV module comprising at least one venting module configured to introduce air selected from a group consisting of: heated air, cooled air room temperature air and any combination thereof into the ANTI.

According to another embodiment of the invention, a method as defined above is disclosed, additionally comprising a step of selecting the TRV comprising a feedback mechanism for the air quality selected from a group consisting of: temperature, humidity, airborne particle content, gas concentration, and any combination thereof, configured to maintain the quality in a predetermined value or value range.

According to another embodiment of the invention, a method as defined above is disclosed, wherein the TRV is a fan rotating perpendicularly to a rotor's shaft, and further wherein the shaft is positioned in parallel to the ANTI's main longitudinal axis.

According to another embodiment of the invention, a method as defined above is disclosed, additionally comprising a step of attaching air turbulating means (ATM) adjacently to the TRV for slowing and moderating the airflow stream.

According to another embodiment of the invention, a method as defined above is disclosed, additionally comprising a step of attaching at least one first TRV to one of the ends and at least one second TRV located to the opposite end.

According to another embodiment of the invention, a method as defined above is disclosed, additionally comprising a step of air communicating with the ANTI at least one air recycling mechanism (ARM); comprising: (a) at least one air inlet for collecting air stream from the ANTI's outer environment; (b) at least one recycled-air outlet for collecting air streamed from the ANTI's inner environment; and, (c) at least one air inlet introducing air towards the ANTI's inner environment throughout the TRV.

According to another embodiment of the invention, a method as defined above is disclosed, additionally comprising a step of attaching to at least one air flow regulator to the ANTI for regulating at least one air stream selected from a group consisting of the recycled air stream, the air stream from the ANTI's outer environment, the air streamed towards the ANTI's inner environment, and any combination thereof.

According to another embodiment of the invention, a method as defined above is disclosed, additionally comprising a step of selecting the ANTI, the TRV or both comprising at least one air filter.

According to another embodiment of the invention, a method as defined above is disclosed, additionally comprising a step of configuring the ANTI to direct the airflow drift generated by the TRV to bypass the location of the neonate residing within.

According to another embodiment of the invention, a method as defined above is disclosed, additionally comprising a step of selecting the ANTI comprising at least one air channel, configured to direct the airflow within the ANTI.

According to another embodiment of the invention, a method as defined above is disclosed, additionally comprising a step of selecting the ANTI configured to have an air flow of X per volume W and time Y. Air flow volume is measured by Cubic Feet per Minute (CFM).

According to another embodiment of the invention, a method as defined above is disclosed, additionally comprising a step of configuring the air flow parameters of X, W, and Y by the user.

The term "W", "X", and "Y" each represent any positive number. As a non-limiting example the air flow values can range between 0.0001-100 CFM.

According to another embodiment of the invention, at least one of the following parameters: particle count, bacteria count, Air pressure differences, air flow volume and air flow velocity are tested and comply with the standards of procedure as per ISO 14644. As depicted in "Supplementary training modules on Good Manufacturing Practice" for "Heating, Ventilation and Air-Conditioning" published by the world health organization, as long as the outcome meets the standard of IEC 60601-2-19 establishing operating specifications for neonatal incubators. Measuring volume flow can be accomplished in several ways: Performing duct traverses with a thermoanemometer or micromanometer with a probe and then doing the necessary conversions, or using a capture hood directly on the supply diffuser or exhaust grille, or on the vent air exit point.

According to another embodiment of the invention, a method as defined above is disclosed, additionally comprising a step of selecting the ANTI comprising sound attenuating means.

According to another embodiment of the invention, a method as defined above is disclosed, additionally comprising a step of configuring the sound generating means to at least partially muffle the sound generated by a selected from a group consisting of: the TRV, sound generated by air movement within the ANTI, sounds generated by the MRD, and any combination thereof.

According to another embodiment of the invention, a method as defined above is disclosed, additionally comprising a step of configuring at least one resonator to reflect the sound waves so as to cancel out frequencies generated by the air flow and/or vent.

According to another embodiment of the invention, a method as defined above is disclosed, additionally comprising a step of selecting the ANTI, the TRV or both comprising connections configured to at least partially absorb vibration.

According to another embodiment of the invention, a method as defined above is disclosed, additionally comprising a step of connecting the ANTI to the TRV by flexible vibration absorptive materials, connectors or both.

According to another embodiment of the invention, a method as defined above is disclosed, additionally comprising a step of connecting the ANTI, the TRV or both to externally supplied pressurized gas.

According to another embodiment of the invention, a method as defined above is disclosed, additionally comprising steps of: (a) creating a cross section perpendicular to the main longitudinal axis with a central portion and a peripheral portion, adjacent to the ANTI's walls; and, (b) attaching to the ANTI at least one air baffler at at least one position, the position is selected from a group consisting of one end, being either proximal or distal, the opposite end, and any combination thereof; at least one air baffler is positioned within the ANTI at or adjacent to the ANTI's central portion thereby providing between the baffler and the walls apertures for the air to flow along the main longitudinal axis.

According to another embodiment of the invention, a method as defined above is disclosed, additionally comprising a step of arranging at least a portion of the ANTI's walls as double jacket walls (DJW) comprising a perforated inner-wall and an intact non-perforated outer-wall, thereby the DJW is facilitating the air stream, along the main longitudinal axis in a conduit having a predefined width (w) and length (1).

According to another embodiment of the invention, a method as defined above is disclosed, additionally comprising a step of shaping the conduits with equal the width and the length (w, l) along the longitudinal axis.

According to another embodiment of the invention, a method as defined above is disclosed, additionally comprising a step of shaping the conduits with changing of the width and the length (w, l) along the longitudinal axis.

According to another embodiment of the invention, a method as defined above is disclosed, additionally comprising a step of shaping at least one portion of the ANTI along the longitudinal axis so the width (W) in ANTI's upper wall is $W_1$ in its proximal side, $W_2$ in its distal side, and in ANTI's lower wall the width is $W_3$ in its proximal side, $W_4$ in its distal side; at least one of the following is held true: (a) $W_1$ is larger than $W_2$ and $W_3$ is larger than $W_4$; (b) $W_1$ is larger than $W_2$ and $W_3$ is smaller than $W_4$; $W_1$ is smaller than $W_2$ and $W_3$ is smaller than $W_4$; (d) $W_1$ is smaller than $W_2$ and $W_3$ is larger than $W_4$; (e) $W_1$ is larger than $W_3$ and $W_2$ is larger than $W_4$; (f) $W_1$ is larger than $W_3$ and $W_2$ is smaller than $W_4$; (g) $W_1$ is smaller than $W_3$ and $W_2$ is smaller than $W_4$; and, (h) $W_1$ is smaller than $W_3$ and $W_2$ is larger than $W_4$.

According to another embodiment of the invention, a method as defined above is disclosed, manufacturing the ANTI at least partially of MRI-safe materials.

According to another embodiment of the invention, a method as defined above is disclosed, additionally comprising a step of forming at least a portion of the ANTI, the TRV or both of MRI-safe materials.

According to another embodiment of the invention, a method as defined above is disclosed, additionally comprising a step of forming at least a portion of the ANTI comprising materials selected from a group consisting of: vibration absorptive, sound absorptive, liquid resistant, fire resistant, recyclable materials, disposable materials, and any combination thereof.

According to another embodiment of the invention, a method as defined above is disclosed, additionally comprising a step of selecting the ANTI with at least one sensor selected from a group consisting of: a temperature sensor, a motion sensor, a breathing sensor, a gas concentration sensor, an air low sensor, a humidity sensor, a door opening or closing sensor, a weight sensor, an RF sensor, and any combination thereof.

According to another embodiment of the invention, a method as defined above is disclosed, additionally comprising a step of configuring the sensors to relay sensed information to a CPU, an indicator, or both.

According to another embodiment of the invention, a method as defined above is disclosed, additionally comprising a step of selecting the ANTI comprising a central processing unit (CPU).

According to another embodiment of the invention, a method as defined above is disclosed, additionally comprising a step of configuring the CPU to a selected from a group consisting of: control the vent, control the vent by responding to signals received from at least one sensor, control the vent according to values defined by the user, control the vent according to predefined physical condition of the neonate, and any combination thereof.

According to another embodiment of the invention, a method as defined above is disclosed, additionally comprising a step of selecting the TRV comprising an emergency shut-down mechanism.

According to another embodiment of the invention, a method as defined above is disclosed, additionally comprising a step of selecting the ANTI comprising at least one aperture configured to be reversibly opened/closed. Further comprising a step of opening or closing the aperture.

According to another embodiment of the invention, a method as defined above is disclosed, additionally comprising a step of interconnecting the ANTI is to a mobile base by at least one support, thereby forming a mobile thermo-regulated transportable incubator (MTI).

According to another embodiment of the invention, a method as defined above is disclosed, additionally comprising a step of selecting the mobile base and at least one support made of MRI safe material.

According to another embodiment of the invention, a method as defined above is disclosed, additionally comprising a step of selecting the MTI is configured to be at least partially inserted within an MRD bore; further comprising a step of inserting at least a portion of the MTI into an MRD bore.

According to another embodiment of the invention, a method as defined above is disclosed, additionally comprising a step of selecting the TRV venting module located at a selected from a group consisting of: the mobile base, at least one support, at least one ANTI end, and any combination thereof; further wherein connecting the venting module to the ANTI by at least one tubing.

According to another embodiment of the invention, a method for magnetic resonance imaging (MRI) of neonates, comprising the steps of: (a) obtaining an elongated, active, thermo-regulated neonatal transportable incubator (ANTI) having a main longitudinal axis with a proximal end and an opposite distal end comprising in at least one of the ends a temperature regulating vent (TRV), and an MRD comprising an open bore, along the axis; (b) accommodating the neonate in the ANTI, parallel to the axis; (c) thermo regulating the ANTI by the TRV; and, (d) inserting the ANTI into the MRD bore, and imaging, wherein step (c) additionally comprising streaming air by the TRV from the ANTI end towards the opposite end substantially along the axis; further wherein step (d) additionally comprising inserting the ANTI into the MRD bore such that the neonate is parallel to the MRD longitudinal axis.

According to another embodiment of the invention, a method as defined above is disclosed, additionally comprising a step of configuring the ANTI by means of size and shape to be inserted into an MRD having an open bore in its longitudinal axis, and a patient table within the open bore; further comprising a step of configuring the ANTI to: (a) accommodate the neonate, within the bore, parallel to the MRD bore; and, (b) accommodate the neonate in proximity to the MRD patient table.

According to another embodiment of the invention, a method as defined above is disclosed, additionally comprising a step of selecting the TRV from a group of modules consisting of at least one first venting module, at least one first heating/cooling module, at least one filter located adjacently to either the first venting module or the first heating/cooling module and any combination thereof.

According to another embodiment of the invention, a method as defined above is disclosed, additionally comprising a step of selecting the TRV module comprising at least one venting module configured to introduce air selected from a group consisting of: heated air, cooled air room temperature air and any combination thereof into the ANTI.

According to another embodiment of the invention, a method as defined above is disclosed, additionally comprising a step of selecting the TRV comprising a feedback mechanism for the air quality selected from a group consisting of: temperature, humidity, airborne particle content, gas concentration, and any combination thereof, configured to maintain the quality in a predetermined value or value range.

According to another embodiment of the invention, a method as defined above is disclosed, wherein the TRV is a fan rotating perpendicularly to a rotor's shaft, and further wherein the shaft is positioned in parallel to the ANTI's main longitudinal axis.

According to another embodiment of the invention, a method as defined above is disclosed, additionally comprising a step of attaching air turbulating means (ATM) adjacently to the TRV for slowing and moderating the airflow stream.

According to another embodiment of the invention, a method as defined above is disclosed, additionally comprising a step of attaching at least one first TRV to one of the ends and at least one second TRV located to the opposite end.

According to another embodiment of the invention, a method as defined above is disclosed, additionally comprising a step of air communicating with the ANTI at least one air recycling mechanism (ARM); comprising: (a) at least one air inlet for collecting air stream from the ANTI's outer environment; (b) at least one recycled-air outlet for collecting air streamed from the ANTI's inner environment; and, (c) at least one air inlet introducing air towards the ANTI's inner environment throughout the TRV.

According to another embodiment of the invention, a method as defined above is disclosed, additionally comprising a step of attaching to at least one air flow regulator to the ANTI for regulating at least one air stream selected from a group consisting of the recycled air stream, the air stream from the ANTI's outer environment, the air streamed towards the ANTI's inner environment, and any combination thereof.

According to another embodiment of the invention, a method as defined above is disclosed, additionally comprising a step of selecting the ANTI, the TRV or both comprising at least one air filter.

According to another embodiment of the invention, a method as defined above is disclosed, additionally comprising a step of configuring the ANTI to direct the airflow drift generated by the TRV to bypass the location of the neonate residing within.

According to another embodiment of the invention, a method as defined above is disclosed, additionally comprising a step of selecting the ANTI comprising at least one air channel, configured to direct the airflow within the ANTI.

According to another embodiment of the invention, a method as defined above is disclosed, additionally comprising a step of selecting the ANTI configured to have an air flow of X per volume W and time Y.

According to another embodiment of the invention, a method as defined above is disclosed, additionally comprising a step of configuring the air flow parameters of X, W, and Y by the user.

According to another embodiment of the invention, a method as defined above is disclosed, additionally comprising a step of selecting the ANTI comprising sound attenuating means.

According to another embodiment of the invention, a method as defined above is disclosed, additionally comprising a step of configuring the sound generating means to at least partially muffle the sound generated by a selected from a group consisting of: the TRV, sound generated by air movement within the ANTI, sounds generated by the MRD, and any combination thereof.

According to another embodiment of the invention, a method as defined above is disclosed, additionally comprising a step of configuring at least one resonator to reflect the sound waves so as to cancel out frequencies generated by the air flow and/or vent.

According to another embodiment of the invention, a method as defined above is disclosed, additionally comprising a step of selecting the ANTI, the TRV or both comprising connections configured to at least partially absorb vibration.

According to another embodiment of the invention, a method as defined above is disclosed, additionally comprising a step of connecting the ANTI to the TRV by flexible vibration absorptive materials, connectors or both.

According to another embodiment of the invention, a method as defined above is disclosed, additionally comprising a step of connecting the ANTI, the TRV or both to externally supplied pressurized gas.

According to another embodiment of the invention, a method as defined above is disclosed, additionally comprising steps of: (a) creating a cross section perpendicular to the main longitudinal axis with a central portion and a peripheral portion, adjacent to the ANTI's walls; and, (b) attaching to the ANTI at least one air baffler in at least one position, the position is selected from a group consisting of one end, being either proximal or distal, the opposite end, and any combination thereof; at least one air baffler is positioned within the ANTI at or adjacent to the ANTI's central portion, thereby providing between the baffler and the walls apertures for the air to flow along the main longitudinal axis.

According to another embodiment of the invention, a method as defined above is disclosed, additionally comprising a step of arranging at least a portion of the ANTI's walls as double jacket walls (DJW) comprising a perforated inner-wall and an intact non-perforated outer-wall, thereby the DJW is facilitating the air stream, along the main longitudinal axis in a conduit having a predefined width (w) and length (1).

According to another embodiment of the invention, a method as defined above is disclosed, additionally comprising a step of shaping the conduits with equal the width and the length (w, l) along the longitudinal axis.

According to another embodiment of the invention, a method as defined above is disclosed, additionally comprising a step of shaping the conduits with changing of the width and the length (w, l) along the longitudinal axis.

According to another embodiment of the invention, a method as defined above is disclosed, additionally comprising a step of shaping at least one portion of the ANTI along the longitudinal axis so the width (W) in ANTI's upper wall is $W_1$ in its proximal side, $W_2$ in its distal side, and in ANTI's lower wall the width is $W_3$ in its proximal side, $W_4$ in its distal side; at least one of the following is held true: (a) $W_1$ is larger than $W_2$ and $W_3$ is larger than $W_4$; (b) $W_1$ is larger than $W_2$ and $W_3$ is smaller than $W_4$; (c) $W_1$ is smaller than $W_2$ and $W_3$ is smaller than $W_4$; (d) $W_1$ is smaller than $W_2$ and $W_3$ is larger than $W_4$; (e) $W_1$ is larger than $W_3$ and $W_2$ is larger than $W_4$; (f) $W_1$ is larger than $W_3$ and $W_2$ is smaller than $W_4$; (g) $W_1$ is smaller than $W_3$ and $W_2$ is smaller than $W_4$; and, (h) $W_1$ is smaller than $W_3$ and $W_2$ is larger than $W_4$.

According to another embodiment of the invention, a method as defined above is disclosed, manufacturing the ANTI at least partially of MRI-safe materials.

According to another embodiment of the invention, a method as defined above is disclosed, additionally comprising a step of forming at least a portion of the ANTI, the TRV or both of MRI-safe materials.

According to another embodiment of the invention, a method as defined above is disclosed, additionally comprising a step of forming at least a portion of the ANTI comprising materials selected from a group consisting of: vibration absorptive, sound absorptive, liquid resistant, fire resistant, recyclable materials, disposable materials, and any combination thereof.

According to another embodiment of the invention, a method as defined above is disclosed, additionally comprising a step of selecting the ANTI with at least one sensor selected from a group consisting of: a temperature sensor, a motion sensor, a breathing sensor, a gas concentration sensor, an air low sensor, a humidity sensor, a door opening or closing sensor, a weight sensor, an RF sensor, and any combination thereof.

According to another embodiment of the invention, a method as defined above is disclosed, additionally comprising a step of configuring the sensors to relay sensed information to a CPU, an indicator, or both.

According to another embodiment of the invention, a method as defined above is disclosed, additionally comprising a step of selecting the ANTI comprising a central processing unit (CPU).

According to another embodiment of the invention, a method as defined above is disclosed, additionally comprising a step of configuring the CPU to a selected from a group consisting of: control the vent, control the vent by responding to signals received from at least one sensor, control the vent according to values defined by the user, control the vent according to predefined physical condition of the neonate, and any combination thereof.

According to another embodiment of the invention, a method as defined above is disclosed, additionally comprising a step of selecting the TRV comprising an emergency shut-down mechanism.

According to another embodiment of the invention, a method as defined above is disclosed, additionally comprising a step of selecting the ANTI comprising at least one aperture configured to be reversibly opened/closed. Further comprising a step of opening or closing the aperture.

According to another embodiment of the invention, a method as defined above is disclosed, additionally comprising a step of interconnecting the ANTI is to a mobile base by at least one support, thereby forming a mobile thermo-regulated transportable incubator (MTI).

According to another embodiment of the invention, a method as defined above is disclosed, additionally comprising a step of selecting the mobile base and at least one support made of MRI safe material.

According to another embodiment of the invention, a method as defined above is disclosed, additionally comprising a step of selecting the MTI is configured to be at least partially inserted within an MRD bore; further comprising a step of inserting at least a portion of the MTI into an MRD bore.

According to another embodiment of the invention, a method as defined above is disclosed, additionally comprising a step of selecting the TRV venting module located at a selected from a group consisting of: the mobile base, at least one support, at least one ANTI end, and any combination thereof; further wherein connecting the venting module to the ANTI by at least one tubing.

According to another embodiment of the invention, a standard of care for thermo-regulating a neonate, comprising steps of: (a) obtaining an elongated active thermo-regulated neonatal transportable incubator (ANTI) having a main longitudinal axis with a proximal end and an opposite distal end; (b) attaching to the at least one of the ends a temperature regulating vent (TRV); (c) accommodating the neonate in the ANTI parallel to the axis; and, (d) thermo-regulating the ANTI by the TRV; wherein the step (d) additionally comprising streaming air by the TRV from the ANTI end towards the opposite end substantially along the axis; further wherein at least one of the following is held true: (a) the noise level in the ANTI is below 60 Decibels; (b) the noise level in the ANTI is below 45 Decibels (c) the temperature in the ANTI is at most 2° C. higher or lower from the set temperature; (d) the $CO_2$ concentration within the ANTI does not exceed 4%; (e) the $O_2$ concentration within the ANTI does not fall below 30 vol. %, and does not exceed 40 vol. %; (f) the air velocity over the mattress within the ANTI does not exceed 0.35 m/s; (g) the amount of thermoregulation related complications of neonates when utilizing the ANTI is b times lower than the average value of thermo-regulation complications of neonates; b is equal or greater than 1.05; (h) the average value of salivary cortisol level index from noise derived stress of patient when utilizing the ANTI during MRI is n times lower than the average value during MRI; n is equal or greater than 1.05; (i) the average number of MRI repetition number per patient is p times lower when utilizing the ANTI than the average number of MRI repetitions during MRI of patients; p is equal or greater than 1.05; (j) the average value of salivary cortisol level index from open space related stress of patient when utilizing the ANTI during MRI is q times lower than the average the value during MRI; q is equal or greater than 1.05; (k) the ANTI will continue to be used safely in occurrence of a leakage of up to 200 ml deposited in the inner volume of the ANTI; (l) the ANTI will remain stable when tilted 10° in normal use and when tilted 20° during transportation; (m) the ANTI will not tip over when the force is 100 N or less; (n) the average number of patients MRI related fall incidents when utilizing the ANTI is r times lower than the average of patients MRI related fall incidents; r is equal or greater than 1.05; (o) the radiated electromagnetic fields in the inner volume of the ANTI, comprising electrical equipment system will be at a level up to 3 V/m for the frequency range of the collateral standard for EMC (electromagnetic compatibility); further the electrical equipment is performing its intended function as specified by the manufacturer or fail without creating a safety harm at a level up to 10 V/m for the frequency range of the collateral standard for EMC; and, (p) the average number of insurable claims of a selected from a group consisting of: manufacturer, handler, user, operator, medical care personal, medical facility, medical facility management or any combination thereof when utilizing the ANTI is v times lower than patient MRI associated insurable claims; v is equal or greater than 1.05.

Reference is now made to FIG. 1a, illustrating in a non-in-scale manner an example of prior art of an ANTI with a TRV located at the bottom; this kind of ANTI is recited in U.S. Pat. No. 6,511,414. In this setting, air flows upwardly in a non-direct manner and therefore is forced to have kinks. This kind of indirect flow is necessarily less discreet (noisy) then direct flow. Indiscreet airflow may exceed the allowed volume inside an incubator which is no more than 60 decibels or preferably no more than 45 decibels. In addition, this type of TRV located at the bottom, below the neonate, necessarily forces the placement of the neonate to rise above the originally designated patient location within an MRI bore. As a consequence the neonate dose not reside in the accurate location in reference to the magnetic field, and the quality of the image received decreases. This is especially true for magnetic resonance devices comprising permanent magnet installations, having the main magnets stationed above and below the patient location. The stationed magnets define the direction of the homogenous magnetic field. B0 represents the constant, homogeneous magnetic field used to polarize spins, creating magnetization. The direction of B0 defines the longitudinal axis that perpendicular to it the RF pulse applied deflects the net of the magnetic field. B0 can refer to both the direction and the magnitude of the field. The main magnets are especially placed in reference to the originally designed patient placement to allow the exact location of the isocenter of the magnetic field.

As these magnetic resonance devices allow for limited scanning in the axis, perpendicular to the patient table, they provide no such limitation at the axis parallel to the patient table, allowing for an extra length in the longitudinal axis of the MRD bore without compromising the image quality. Further, transportable incubators having a TRV at the top or bottom are not always fitted by means of size and shape into an MRD bore and are therefore not appropriate for scanning neonates in all the MRDs known in the art.

Reference is now made to FIG. 1b, illustrating in a non-in-scale manner an embodiment of the current invention in which the TRV is located at the proximal end of the ANTI. Thermo-regulated air from the TRV flows through the proximal end of the incubator in parallel to the longitudinal axis of the ANTI. This type of direct air streaming is discreet and can meet the noise requirements of a neonate's incubator. Further, the placement of the TRV at the proximal end maintains the position of the neonate in reference to the patient table in the MRD bore, thereby not interfering with the imaging process.

Figure 2A:
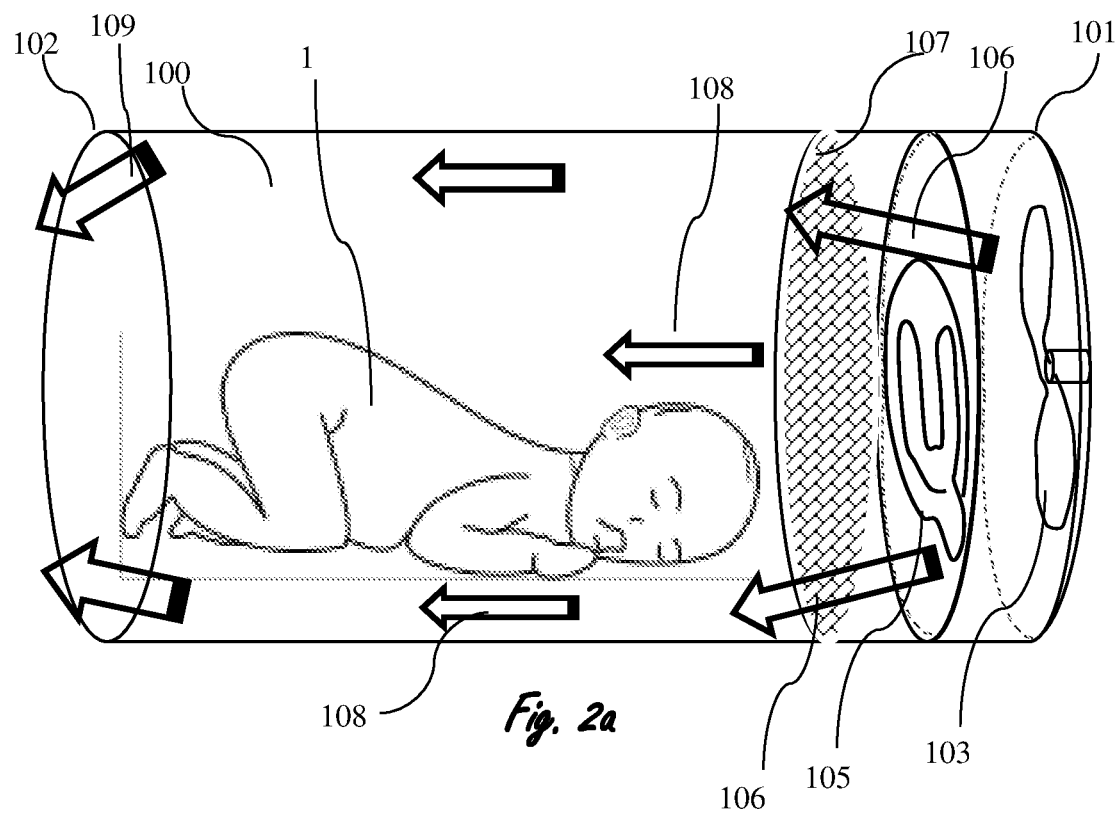
FIG. 2a and FIG. 2b, each of which is illustrating in a non-in-scale manner a partially perspective side view of active-thermo-regulated neonatal transportable incubator (ANTI) (100)
Figure 2B:
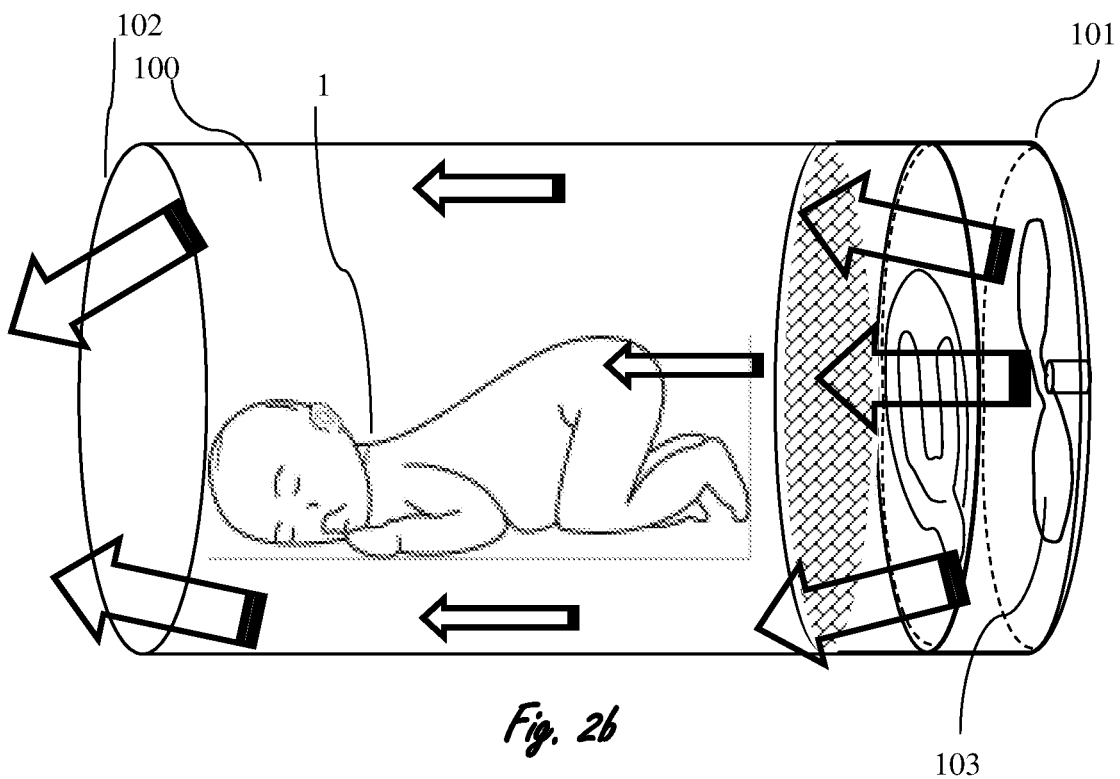

Reference is now made to FIG. 2a and FIG. 2b, each of which is illustrating in a non-in-scale manner a perspective view of an active neonate transportable incubator (ANTI) (100). The ANTI (100) is an elongated container of predefined size, shape and cross-section, encapsulating an inner thermo-regulated close environment having a proximal side (101) and a distal side (102) at the ends of the longitudinal axis of the elongated container. According to an embodiment of the invention, a temperature regulating vent (TRV) is in fluid communication with the proximal side, and comprising at least one first fluid venting module, e.g., a fan, a jet, a blower, a compressor, a pump etc. or any combination of the same (103) and at least one first fluid heating/cooling module (e.g., an air conditioned system, an infrared heater, a water/oil-heated radiator, a coiled heater, an open coil air heater, a round open coil air heater, a convection heater, straight or formed tubular heaters, a quartz tube air heater, a capacitor-type heater, a Pelletier module or any combination of the same) is located (105). Distally (and/or proximally) to the TRV at least one first filter is located (106). Neonate (1) is positioned head-wise (FIG. 2a) or leg-wise (FIG. 2b) to the TRV. The TRV is operative in a method, e.g., where airflow (106) is facilitated from proximal end (101) by fan (103) towards heater (105). The airflow is streamed via filter (106) to the inner environment of the incubator. A gentle yet effective thermo-regulated airflow (108) is facilitated from the inner environment to the outside environment, via e.g., opening at the distal end (see flow 109). The airflow is parallel to the longitudinal axis of the ANTI's container and since the TRV is in fluid communication with the proximal end of the axis there is no kinks in the airflow and therefore is very quiet.

Figure 2C:
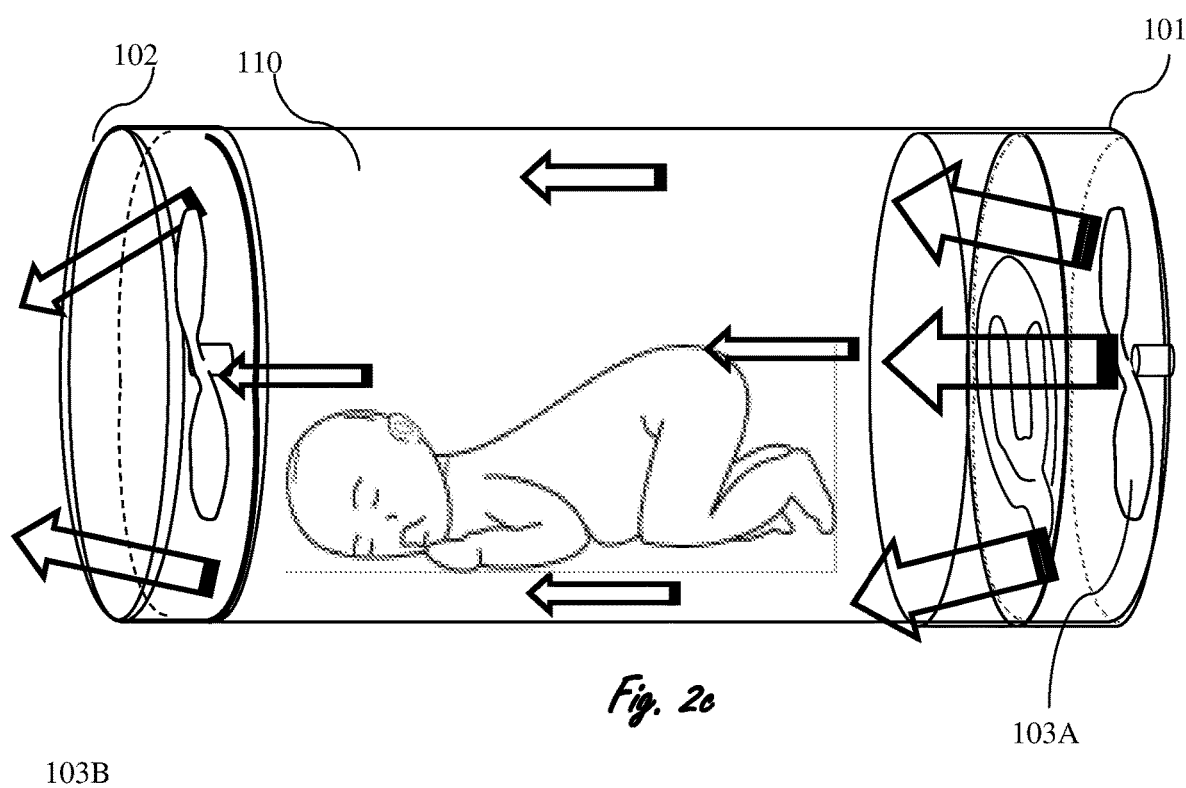
FIG. 2c, illustrating in a non-in-scale manner a partially perspective side view ANTI (110) according to yet another embodiment of the invention, comprising an additional venting module.

Reference is now made to FIG. 2c, illustrating in a non-in-scale manner a partially perspective side view of an ANTI (110) according to yet another embodiment of the invention the ANTI (110) comprises at least one first fan (103A) located at the proximal end of the incubator, and at least one second fan (103B) located at the distal end (102). In this air flow scheme, air is pushed, warmed and filtered by the proximal fluid venting module, and continuously or discreetly pulled by the distal fluid venting module.

Figure 2D:
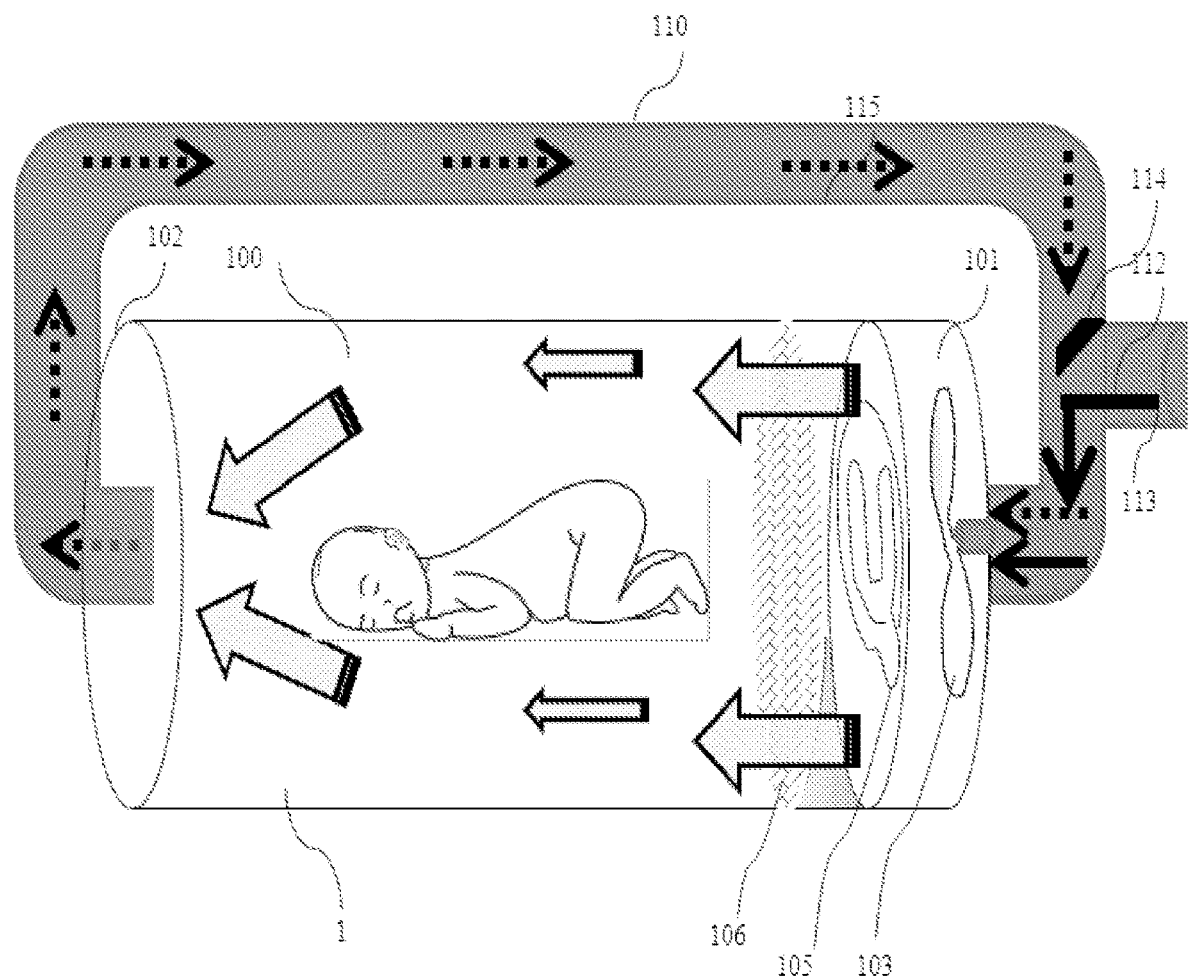
FIG. 2d, illustrating in a non-in-scale manner side view ANTI in which a tube comprising a regulator controls the flow of recycled air from within the incubator and fresh air from the surroundings into the incubator.
Figure 2E:
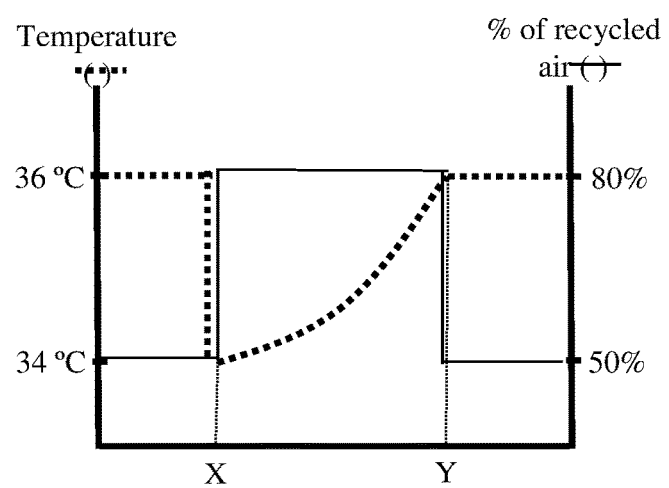
FIG. 2e illustrating in a non-in-scale manner the change of percent of recycled air flowing to the ANTI at different temperatures.

Reference is now made to FIG. 2d, illustrating in a non-in-scale manner side view of an ANTI (100) in which a tube (114) is connecting between the TRV or venting module at the distal end with the TRV at the proximal end. The tube also has an opening towards the surroundings of the ANTI (112). The tube comprises a regulator (114) which controls the amount of air flowing from the distal TRV (warm recycled air) (115) and fresh air (113) from the surroundings into the incubator. The tube flows air discharged from the vent at the proximal end of the ANTI as well as air from the surroundings of the ANTI. The ratio between the amounts of air flown into the ANTI from the two sources is controlled by the regulator. When the ANTI is closed and temperature is kept steady the regulator enables mostly air from the surroundings to flow into the ANTI. This air is rich in oxygen. However, when the ANTI is opened and temperature decreases, the regulator enables flow warm recycled air into the ANTI that although has low concentrations of oxygen, helps re-heating the ANTI. The regulator may enable the flow of mixed air in different ratios according to the degree of the drop in the temperature and the oxygen concentration inside the ANTI Reference is now made to FIG. 2e, illustrating in a non-in-scale manner a graph demonstrating the change in the amount of recycled air flown into the ANTI according to the change of temperature. When the ANTI is closed and temperature is kept steady at 36° C. (before time point X) the amount of recycled air is also kept steady (50% in this example) by the regulator. Once the ANTI is opened (time point X), the temperature inside the ANTI decreases and there is a need to re-heat it as quickly as possible. In response to the temperature change, the regulator increases the amount of recycled air flow from 50% to 80%. Since the recycled air is warm it helps to return the temperature inside the ANTI back to 36° C. Once the temperature stabilizes the regulator decreases the recycled airflow back to 50%.

Reference is now made to FIG. 2f, illustrating in a non-in-scale manner a partially perspective side view of an ANTI (120) according to yet another embodiment of the invention. The ANTI (110) comprises all features of incubator 110, e.g., the venting module (103A) and a heating/cooling module (106) at proximal portion and another venting module (103B) at distal side (109) etc., and one or more air bafflers, here a proximal baffler (121A) and a distal baffler (121B). Airflow (122) facilitated by fan 103A is heated and streamed towards baffler 121A, which is, e.g., a curved member, polygonal member, a texturized surface, a shaped surface comprising one or more apertures etc. Air is thus forced to flow (123) via upper and/or lower apertures (124) provided between the baffler and incubator's wall. Air flows (108) within the ANTI's inner environment substantially in parallel to the ANTI's walls in a linear manner. In this way, air turbulences are eliminated, and thus the neonate (1) is not been subjected to perpendicular air flow. (120). Much similarly, airflow (108) is steamed by fans (e.g., fan 103B) to exit (109) the ANTI by streaming (123) it via a second baffler (121B).

Figure 2G:
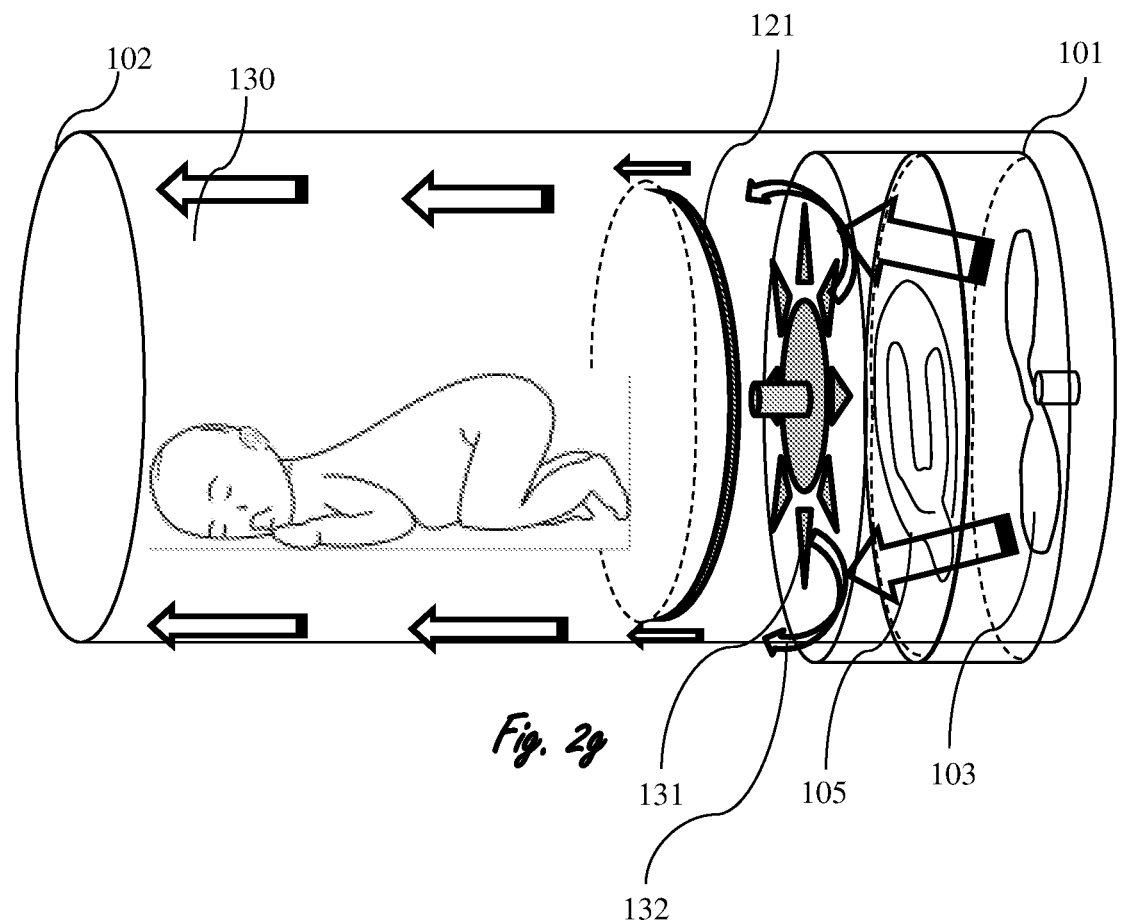
FIG. 2g, illustrating in a non-in-scale manner a partially perspective side view the ANTI (130) according to yet another embodiment of the invention, comprising air turbulating means.

Reference is now made to FIG. 2g, illustrating in a non-in-scale manner a partially perspective side view of an ANTI (130) according to yet another embodiment of the invention. The ANTI (130) comprises a variant of the aforesaid fluid venting module. Here, the venting system comprises at the ANTI's proximal end (101) at least one TRM comprising a venting module (e.g., fan 103), heating/cooling module (105) and a wind baffler (121). In at least one predefined location, e.g., between the heating/cooling module and the baffler, there an air turbulating means is further located (131). This can be a pre-fan or post-fan ventilator adapted to a relatively slow rotation to gentle (132) air stream (105) before or after its baffling. The turbulating means are selected in a non-limiting manner from active members, such as fan, multiple-fan arrangement or cascade thereof, air pump, Dyson-type bladeless air multiplier, venting apparatus etc., and/or passive members, such as texturized strainer, curved conduits in a continuous barrier etc.

Figure 2H:
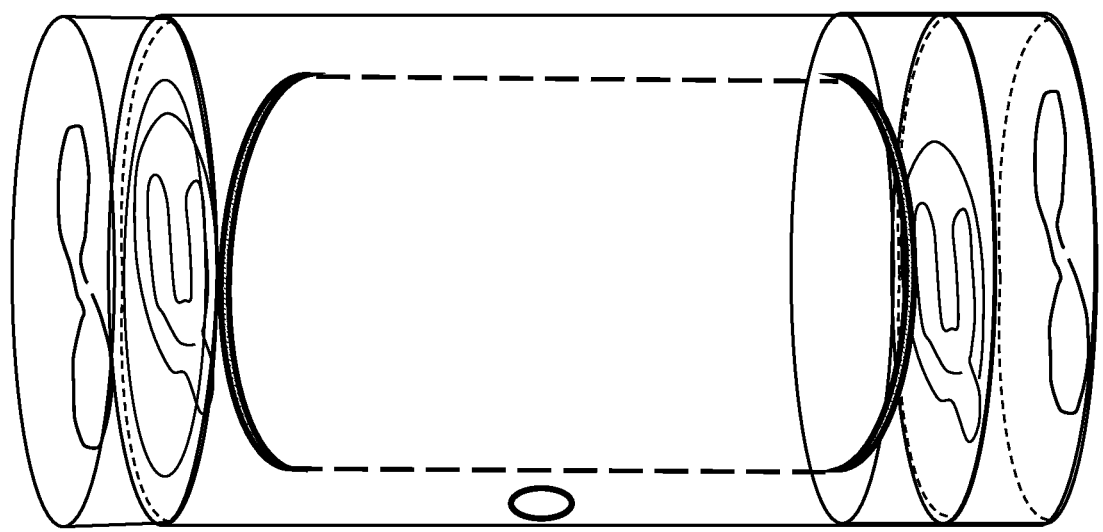
FIG. 2h, illustrating in a non-in-scale manner a partially perspective side view of the ANTI (130) according to yet another embodiment of the invention, comprising at least one orifice.

Reference is now made to FIG. 2h illustrating in a non-in-scale manner a partially perspective side view of the ANTI (130) according to yet another embodiment of the invention, comprising at least one orifice. The orifice may be located in the upper wall of the ANTI, the lower wall (as illustrated) or both. Air flown into the ANTI is streamed out through the orifice(s). The location of the orifice can determine the type of airflow in the ANTI (linear or turbulent).

Figure 2I:
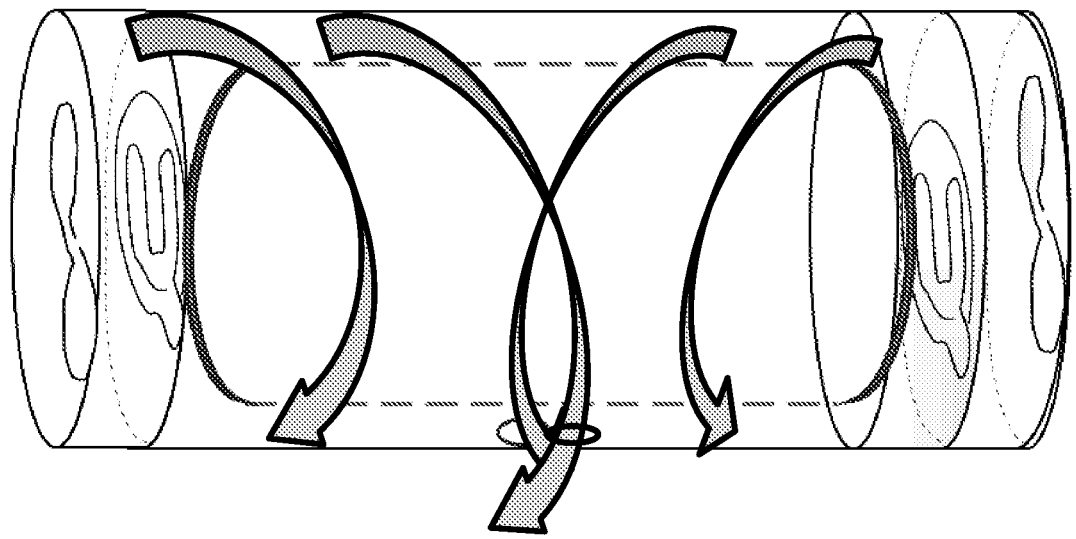
FIG. 2i and FIG. 2j illustrating in a non-in-scale manner a partially perspective side view and front view of linear airflow through apertures between the baffle and the upper part of the ANTI and an orifice in the lower part of the container.
Figure 2J:
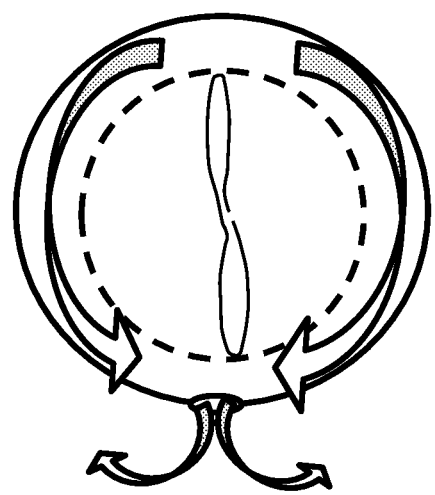

Reference is now made to FIG. 2i and FIG. 1j illustrating in a non-in-scale manner a partially perspective side view and front view of turbulent airflow through apertures between the baffle and the upper part of the container and an orifice in the lower part of the container. In this embodiment, air is flowing through upper apertures created by the baffler and the inner wall of the container. The apertures are located both at the proximal and distal side of the ANTI. An orifice is located at the center of the opposite side to apertures (lower part of the container, in this case). Air flows from the TRV through the apertures and exit through the single orifice. It can be observed that the airflow from both sides clash with each other and therefore flow is turbulent.

Figure 2K:
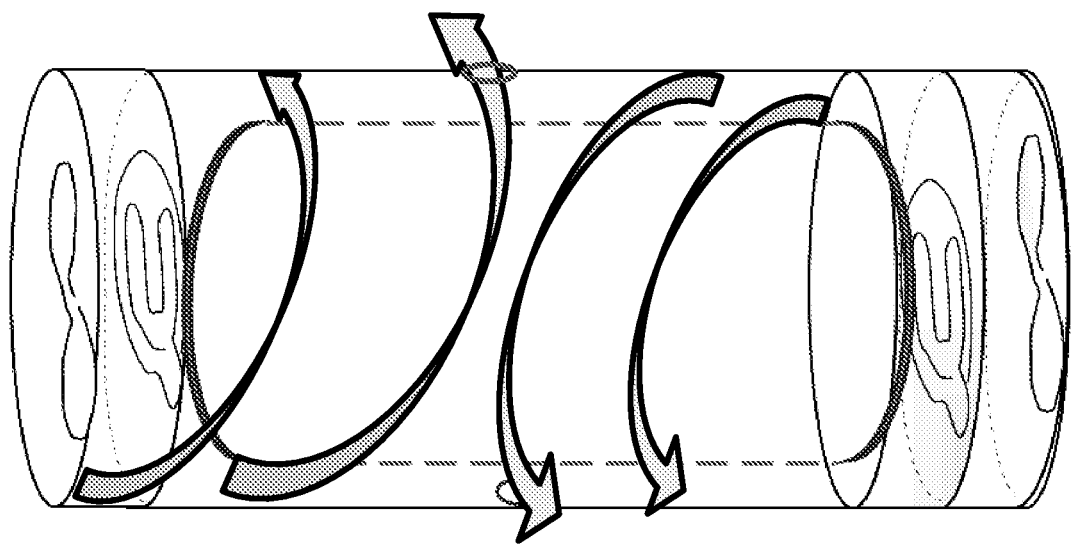
FIG. 2k and FIG. 2l illustrating in a non-in-scale manner a partially perspective side view and front view of linear airflow through an aperture between the baffle and the upper part of the ANTI and an aperture between the baffle and the lower part of the container and through two orifices located in the lower and upper part of the container.
Figure 2L:
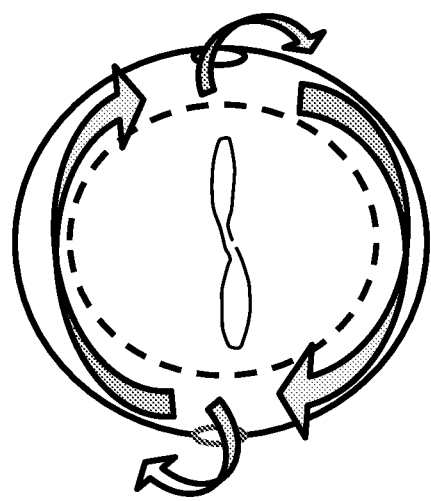

Reference is now made to FIG. 2k and FIG. 2l illustrating in a non-in-scale manner a partially perspective side view and front view of linear airflow through an aperture between the baffle and the upper part of the container and an aperture between the baffle and the lower part of the container and through two orifices located in the lower and upper part of the container. In this embodiment air is flowing from apertures located in opposite directions in the proximal and distal ends of the container. However, the two air streams do not collide as there is an orifice located on each part of the container (upper and lower) and therefore the airflow is linear.

Figure 2M:
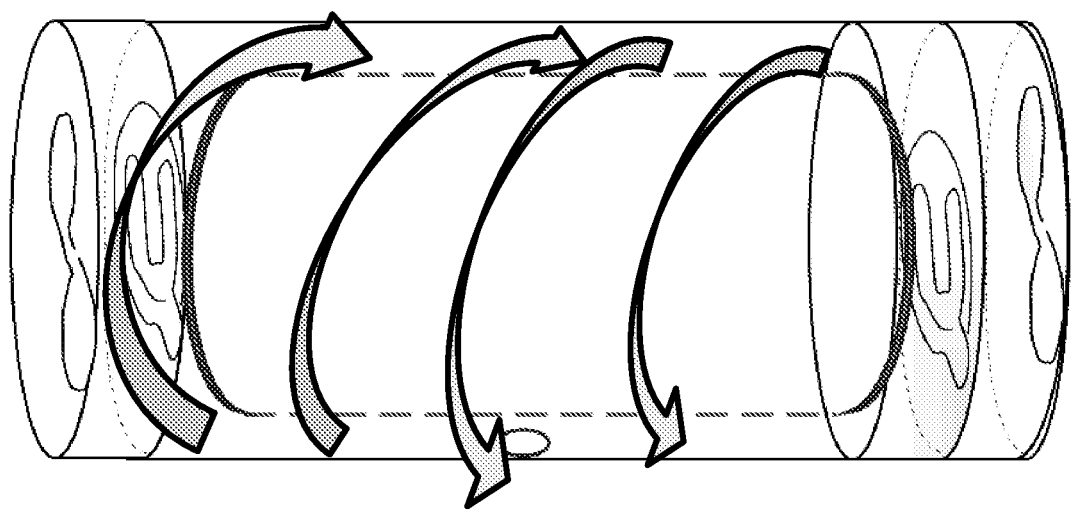
FIG. 2m and FIG. 2n illustrating in a non-in-scale manner a partially perspective side view and front view of turbulent flow through an aperture between the baffle and the upper part of the ANTI and an aperture between the baffle and the lower part of the container and one orifices located in the lower or upper part of the container.
Figure 2N:
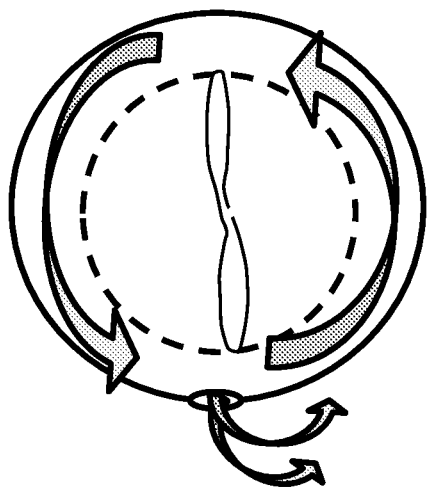

FIG. 2m and FIG. 2n illustrating in a non-in-scale manner another partially perspective side view and front view of linear flow where air flows through an aperture between the baffler and the upper part of the container and an aperture between the baffle and the lower part of the container and one orifices located in the lower or upper part of the container. However, the two air streams do not collide as they unite and exit through the one orifice located on the lower part of the container and therefore the airflow is linear.

Figure 2O:
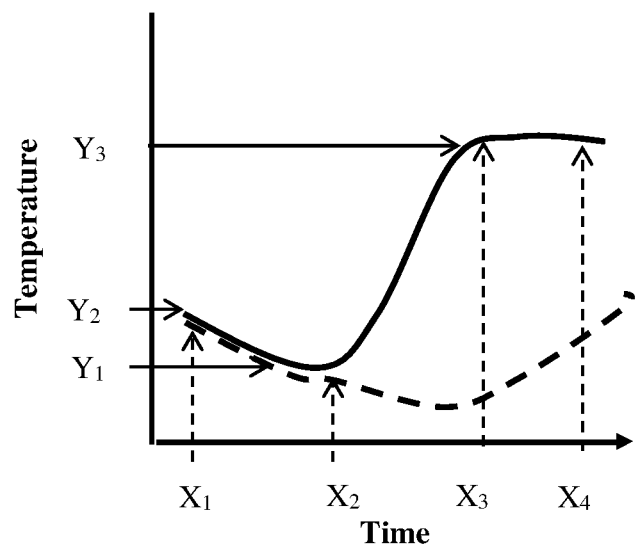
FIG. 2o illustrating in a non-in-scale manner the difference in time ($\Delta T$) for changing the temperature utilizing a linear flow and a turbulent flow.

Reference is now made to FIG. 2o illustrating in a non-in-scale manner the difference in time ($\Delta T$) for changing the temperature utilizing a linear flow and a turbulent flow. The graph in the figure describes the time it takes an ANTI to return to its designated temperature after an event causing a shift in that temperature. $X_1$ represent the time in which an event has occurred (like opening the door of the incubator) which causes a decrease in the temperature (from temperature $Y_2$ which is the designated temperature). Point $X_2$ presents the time in which the TRV starts warming the ANTI. The continuous line represents warming by turbulent flow while the broken line represents warming by linear flow. It can be observed that turbulent flow warms the ANTI environment much faster than linear flow.

Figure 2P:
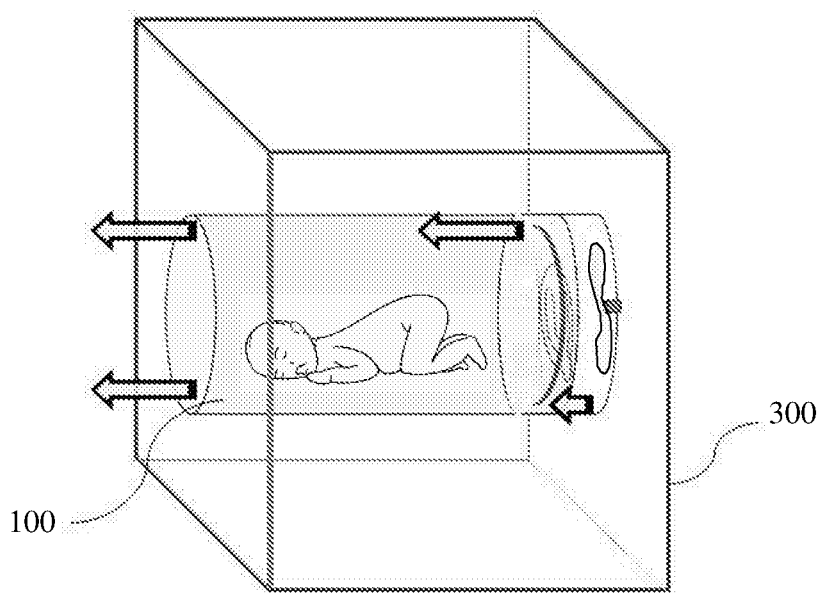
FIG. 2p illustrating in a non-in-scale manner an ANTI accommodated within an MRI bore.

Reference is now made to FIG. 2p illustrating in a non-in-scale manner an ANTI accommodated within an MRI bore. The ANTI has only one plane between its distal and proximal ends. This plane essentially accommodates only the neonate. There is no equipment based above or below the ANTI, which makes it highly suitable for imaging. Similar to FIG. 2p, the ANTI can also be accommodated into a CT scanner, X-ray device or a cart for transporting it. This ANTI provides a solution for thermo-regulating neonates during various examinations they go through.

Reference is now made to FIG. 3, illustrating in a non-in-scale manner a partially perspective side view of an ANTI (200) according to yet another embodiment of the invention. The ANTI (200) comprises a fluid venting module comprising e.g., fan, heater and a proximal baffler (121A). The incubator comprises, within its inner portion, an arrangement of double-jacket walls. Hence, for example, an upper double-wall arrangement comprising an outer envelope (250) and an inner envelope (251). Those inner and outer walls which envelop the infant (l) are layered in a manner that provides an effective air flow (108). The outer wall can be a continuous envelope or at least partially perforated envelope. The inner wall is at least partially perforated. The air-conduit provided by the double jacket walls is characterized by a width (w), w is equal along air conduit (253), namely along the longitudinal axis (101-102), or not equal, to have at least one portion of a small width (w), and at least one portion of relatively large width (W), where W>w.

In one example of such a system, ambient air is streamed from e.g., the proximal end (101) to the e.g., distal end (102) by a fan and thermo-regulated by a heater. It is then continuously or non-continuously forced by a baffler (121A) to a conduit of width (w) provided within the upper (infant's ceiling side) double jacket of wall (250, 251). Inner wall (251) is perforated thereby air is allowed to circulate, evacuating air with respectively high carbon dioxide concentration from the inner environment of the incubator (254) and inflowing air with respectively low carbon dioxide concentration, whilst thermo-regulating the environment (254). Reference is still made FIG. 3, illustrating a lower double jacket (infant's bedside) provided by two concentric parallel layers of non-perforated external wall (260) and perforated inner wall (261) providing liner air flow (108) to an effective yet gentle air circulation (201).

Reference is now made to FIG. 4a, schematically illustrating a cross-section of a portion of the upper (neonate's ceiling side) double jacket of the walls (250, 251) in non-limiting and out-of-scale manners. Here again, thermo-regulated air flow (108) is streamed from the proximal side of the incubator (101). Width (w) is equal along the conduit (253) providing air inflow and outflow (202B, 202A).

Reference is now made to FIG. 4b, schematically illustrating a cross-section of a portion of the upper (infant's ceiling side) double jacket of the walls (250, 251) in non-limiting and out-of-scale manners. Thermo-regulated air flow (108) is streamed from the proximal side of the incubator (101) via conduit (253). Width is varied in a manner that initial width (w) is narrow and then width increases (W). Due to a Venturi effect, high pressure clean and thermo-regulated air stream at the proximal side of the conduit efflux (202A) towards the inner environment of the incubator (254). At the distal portion of the conduit, width (W) is respectively greater, and again, due to a Venturi effect, air influx (202B) into the conduit via the perforated inner wall (251). Conduit 253 expands its width at location 254. Thus, when neonate's mouth is facing location 254, where conduit 253 expands its width, or otherwise located adjacent to the area, carbon dioxide is effectively, silently and safely evacuated from the area surrounding the infant mouth. At the same time, thermo-regulated clean air is forced in a controlled manner to the infant's surroundings at a location located remotely to neonate's head.

Reference is now made to FIG. 4c, schematically illustrating a cross-section of a portion of the upper neonate's ceiling side) the double jacket of the walls (250, 251) in non-limiting and out-of-scale manners. Here again, thermo-regulated air flow (108) is streamed from the proximal side of the ANTI (101) via the conduit (253). Width is varied in a manner that initial width (W) decrease along the conduit to a width (w) due to a Venturi effect which was described above, low pressure stream of air in the proximal side of the conduit evacuate carbon dioxide rich air flow towards the conduit (202B), whilst high pressure air stream at the distal side forces clean and thermo-regulated air flow from the conduit towards the inner environment of the ANTI (254).

Reference made to FIGS. 4b and 4c. Similar to FIGS. 4b and 4c showing changes in the width (w) along the conduit, changes can also occur in the length (l) of the conduit and cause similar Venturi effect.

Figure 5A:
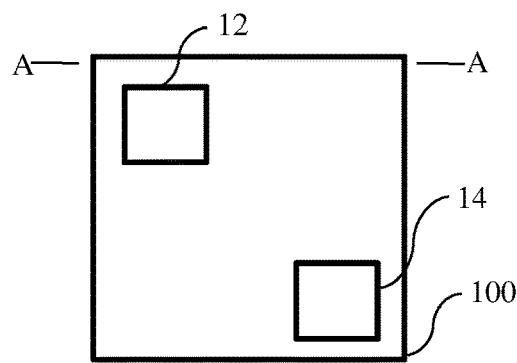
FIG. 5A, and FIG. 5B schematically illustrating a back view and a side view of an actively ventilated and/or thermo-regulated transportable incubator for accommodating a neonate.

Reference is now made to FIG. 5A, schematically illustrating in an out of scale manner a back view of an active transportable incubator (100). Visible is the air entry port (12), and the air exit port (14). Further depicted is the line A-A of the section illustration detailed in FIG. 5B.

Figure 5B:
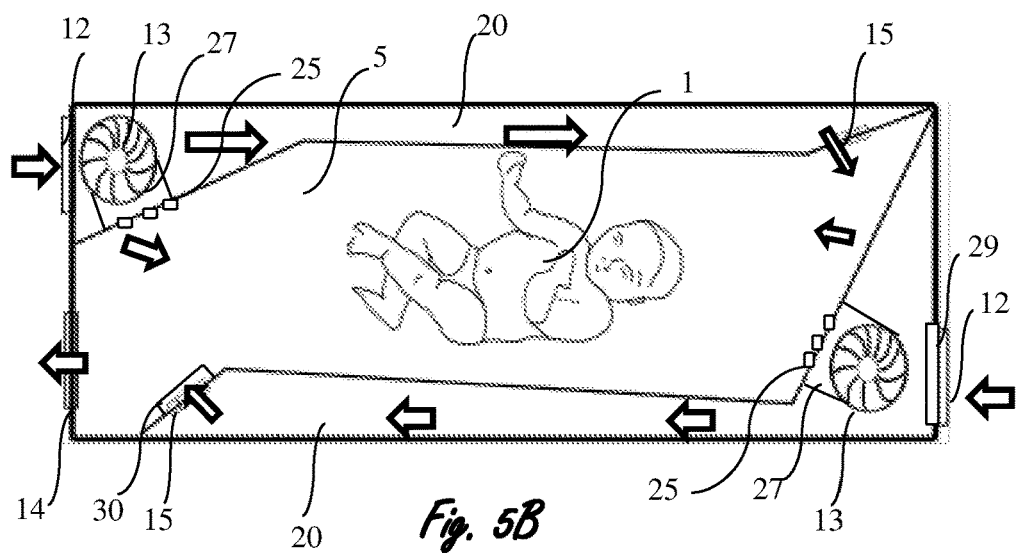

Reference is now made to FIG. 5B, schematically illustrating in an out of scale manner a top section view of an active transportable incubator (100), along the line 'A' in FIG. 5A. In this embodiment, the incubator comprises two TRV's (101, 102). The TRV's can be identical or non-identical, further there can be a single TRV or a plurality thereof. Each TRV (101, 102) includes an air moving device such as a fan (13), a blower, a ventilator and etc. At least one TRV can be connected to any air modifier such as a humidifier, to oxygen supply, to an external heater or cooler. Further the TRV is connected to a CPU (27), configured to control the air flow as preconfigured by the user, or by a feedback mechanism operated by analysis of information received by at least one sensor (25) located within the incubator. The sensed information can be relayed to at least one indicator (an indicator based on sound, light sensation, or any combination thereof), or any user interface such as a screen or computer. Further the sensed information can be transmitted to a communication system such as an internal computer net, the internet, as a message on e-mail or mobile phone SMS, trigger a pager call, any medical monitoring system, or transmitted locally to a monitor or a nurses station. The sensors are configured to sense any of the following: vibration, sound levels, temperature, gas concentration, air flow (air pressure, wind, and etc.), humidity, an incubators door opening and closing, structural integrity of the incubator, whether the incubator is currently housing a patient, and etc. In addition the incubator can include any sensors configured to sense the medical wellbeing of the neonate within (enabling monitoring of such as breathing, cardio-vascular activity, movement, and etc.). The sensors (25) are connected to the CPU (27), to at least one indicator, or both. Each fan (13) is placed within a channel (20), conduit, tubing, corridor, pathway, configured to direct the passage of the air, away from the neonate's (1) head. This channel is a mean of distribution of the air within the incubator insuring the recycling of the air throughout the inner volume of the incubator. Each channel comprises an air entry port (12) facilitating the entrance of air from the outside, and can be connected to an air filter (29). The air filter is configured to filter such as particles in the air, smoke, chemical molecules, humidity, bacteria, dust, and any air borne substance. Each channel further comprises an air exit port (15) that can also comprise an air filter (30). The air filter (30) can be identical to the entry port filter or configured to filter the air of smaller diameter particles or different molecules. The exit port (15) comprises a maneuverable baffle that can change the direction, turbulence, air pressure of the air flown into the inner volume (5). The arrows indicate the air flow from outside the incubator into the inner volume (5) through the TRV's (101). The TRV can be configured to distribute air borne medication in a specific concentration, having control of the dosage also by determining the rate of entry through a TRV, and the rate of recycling the air within the inner volume (5) thereby removing the air borne drug.

Figure 6:
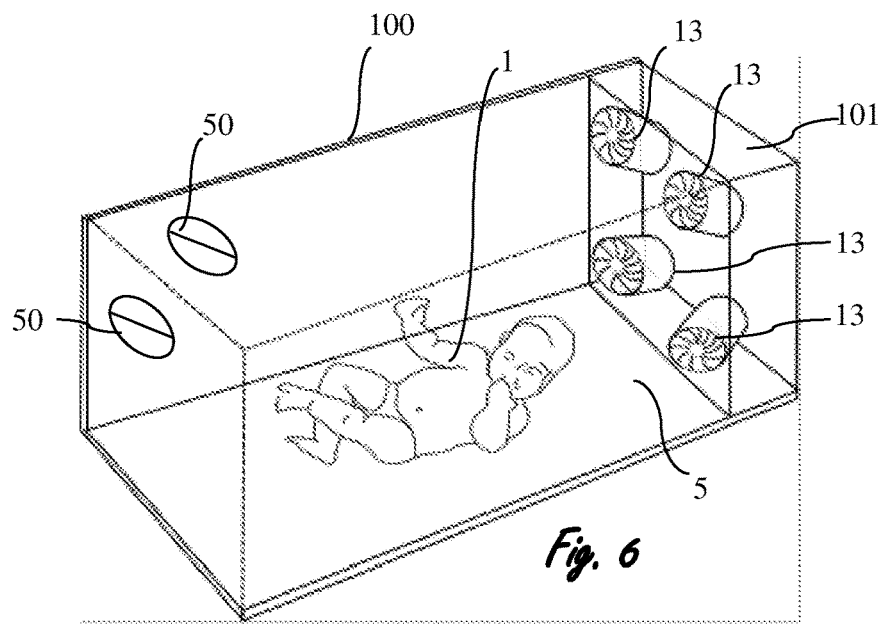
FIG. 6, schematically illustrating a perspective view of an ANTI for accommodating a neonate comprising a TRV including a plurality of vents.

Reference is now made to FIG. 6, schematically illustrating a perspective view of an active transportable incubator (100). The incubator comprises at least one TRV (101), harboring a plurality of ventilators (13), (interchangeable to such as a vent, blower, compressor, fan, multi fan complex, moving flap or sail, or any mean configured to move air). Each ventilator can have a separate air entry port, connected to a separate filter, or vacuum air originating in a common container or tank connected to one common air filter, and optionally connected to externally provided humidity, heating/cooling, gas supply such as compressed air, oxygen and etc. Each fan (13) can be configure to stream air in a different angel. This attribute can be obtained also by a baffle located at the air exit port from the TRV (101) into the incubator (100). In some embodiments the angel of the air flow from the fan (13) can be manipulated to bypass the neonate housed within, or configured to better the distribution of the recycled air in the incubator (100). Further some fans can be directed at moving air into the inner volume (5), while others can be configured to stream the air out. Additionally or alternatively, the incubator has at least one opening for streaming air out side of the incubator. This opening can be a passive one way air flowing port, configured to open as a result of a specific temperature, electrical field, magnetism, humidity, light or exposure to a specific solution (using a material that changes its proportions or properties e.g. flexibility in reaction to temperature for example heat reactive polymers or shape memory polymers, or a thin flexible membrane that passively opens in response to air pressure differences to release the air from within. Also in the scope of the invention is an actively controlled opening that can be opened manually or utilizing external force (engine, electric force and etc.). This opening is configured to open following a predetermined alarm triggered by at least one sensor, or remotely by the user manipulating a remote control or a CPU. Additionally or alternatively, the fans differ in the air temperature, air pressure, humidity, origin, gas concentration, any other air flow parameter and a combination thereof, that they stream into and out of the incubator.

Reference is now made to FIG. 7 schematically illustrating an out of scale example of a TRV (101), in a side section view. In this embodiment, the TRV (101) comprises blades (13) configured to move air attached to a central shaft (11) around which they are rotated. The air enters though a face wall (60) having perforations or openings, and exits by passing through an air filter (19). The direct air flow is blocked by a panel (18) having openings in the periphery allowing the passage of air in the direction of the arrows.

Reference is now made to FIG. 8 schematically illustrating in an out of scale manner an embodiment of the invention in a perspective view. The incubator (100) comprises a TRV (101) including at least one fan (13). The TRV (101) is adjoined to a side channel/tubing (20) located externally to the ANTI. The channel (20) distributes the air through a plurality of ports (50) to various locations along the ANTI (100). The location of the channel on the side of the incubator, and the fan located in at least one distal or proximal end do not interfere with the location of the neonate in relation to the top and bottom main magnets of a magnetic resonance device. The ANTI is configured by means of size and shape to be inserted into an MRD bore. Additionally or alternatively the ANTI includes in one of its ends a user interface connected to a CPU comprising a screen (40), and operating buttons (41). The screen (40) can be a monitoring screen, or an intractable touch screen. The operating buttons (41) are configured to control various aspects of the TRV (101) such as the temperature, humidity, air flow, generating alarms, opening and closing an opening of the incubator, the fan, emergency stop buttons, a release button for the filter, and etc. In an embodiment the TRV (101) is a replaceable module, reversibly attachable to the ANTI (100).

The ANTI is at least partially made of MRI-safe materials, such as glass, composite materials, poly (trimethylene terephthalate) (PTT or likewise PET); poly (methylmethacrylate) (PMMA or likewise PHMMA); polyvinyl chloride (container) or blends based on these plastics. Additionally or alternatively, at least part of the ANTI comprises an at least partially transparent portion enabling at least partial view of the neonate residing within.

According to another embodiment of the invention an ANTI, (100) having all means for standing all applied regulations, especially the following standards and sections thereof: ANSI/AAMI/IEC 60601-2-19:2009 Medical Electrical Equipment—Part 2-19: Particular requirements for the basic safety and essential performance of infant incubators. This standard applies to the basic safety and essential performance of baby incubators. This standard can also be applied to baby incubators used for compensation or alleviation of disease, injury or disability. More specifically this especially applies to sections 201.2 Normative references; 201.4 General requirements; 201.8 Protection against electrical HAZARDS from ME EQUIPMENT; 201.9 Protection against MECHANICAL HAZARDS of ME EQUIPMENT and ME SYSTEMS; 201.10 Protection against unwanted and excessive radiation HAZARDS; 201.11 Protection against excessive temperatures and other HAZARDS; 201.12 Accuracy of controls and instruments and protection against hazardous outputs; 201.13 HAZARDOUS SITUATIONS and fault conditions; 201.14 PROGRAMMABLE ELECTRICAL MEDICAL SYSTEMS (PEMS); 201.15 Construction of ME EQUIPMENT; 201.16 ME SYSTEMS; 201.17 Electromagnetic compatibility of ME EQUIPMENT and ME SYSTEMS; 202 Electromagnetic compatibility—Requirements and tests; 210 Requirements for the development of physiologic closed-loop controllers 201.3.201; Figure 201.101—INFANT SKIN TEMPERATURE measurement; Figure 201.102—Variation of INCUBATOR TEMPERATURE; all incorporated herein in its entirely as a reference.

According to another embodiment of the invention an ANTI, (100) having all means for standing all applied regulations, especially the following standards and sections thereof: ANSI/AAMI/IEC 60601-2-20:2009 Medical Electrical Equipment—Part 2-20: Particular requirements for the basic safety and essential performance of infant transport incubators; and more specifically to section 201.3.201; AIR CONTROLLED TRANSPORT INCUBATOR in which the air temperature is automatically controlled by an air temperature sensor close to a value set by the OPERATOR; 201.3.202 AVERAGE TEMPERATURE average of temperature readings taken at regular intervals at any specified point in the COMPARTMENT achieved during STEADY TEMPERATURE CONDITION; 201.3.203 AVERAGE TRANSPORT INCUBATOR TEMPERATURE average of the INFANT TRANSPORT INCUBATOR TEMPERATURE readings taken at regular intervals achieved during STEADY TEMPERATURE CONDITION; 201.3.204 BABY CONTROLLED TRANSPORT INCUBATOR AIR CONTROLLED TRANSPORT INCUBATOR which has the additional capability of automatically controlling the INCUBATOR air temperature in order to maintain the temperature as measured by a SKIN TEMPERATURE SENSOR according to the CONTROL TEMPERATURE set by the OPERATOR NOTE An INFANT TRANSPORT INCUBATOR operating as a BABY CONTROLLED INCUBATOR is a PHYSIOLOGIC CLOSED-LOOP CONTROLLER as defined in IEC 60601-1-10.; 201.3.205 COMPARTMENT environmentally-controlled enclosure intended to contain an INFANT and with transparent section(s) which allows for viewing of the INFANT; 201.3.206 CONTROL TEMPERATURE, temperature selected at the temperature control; 201.3.207 INFANT PATIENT up to the age of three months and a weight less than 10 kg; 201.3.208 INFANT TRANSPORT INCUBATOR, TRANSPORTABLE ME EQUIPMENT that is equipped with a COMPARTMENT and a TRANSPORTABLE electrical power source with the means to control the environment of the INFANT primarily by heated air within the COMPARTMENT; 201.3.209 SKIN TEMPERATURE, temperature of the skin of the INFANT at a point on which the SKIN TEMPERATURE SENSOR is placed; 201.3.210 SKIN TEMPERATURE SENSOR sensing device intended to measure the INFANT'S SKIN TEMPERATURE, all incorporated herein in its entirely as a reference.

Figure 9:
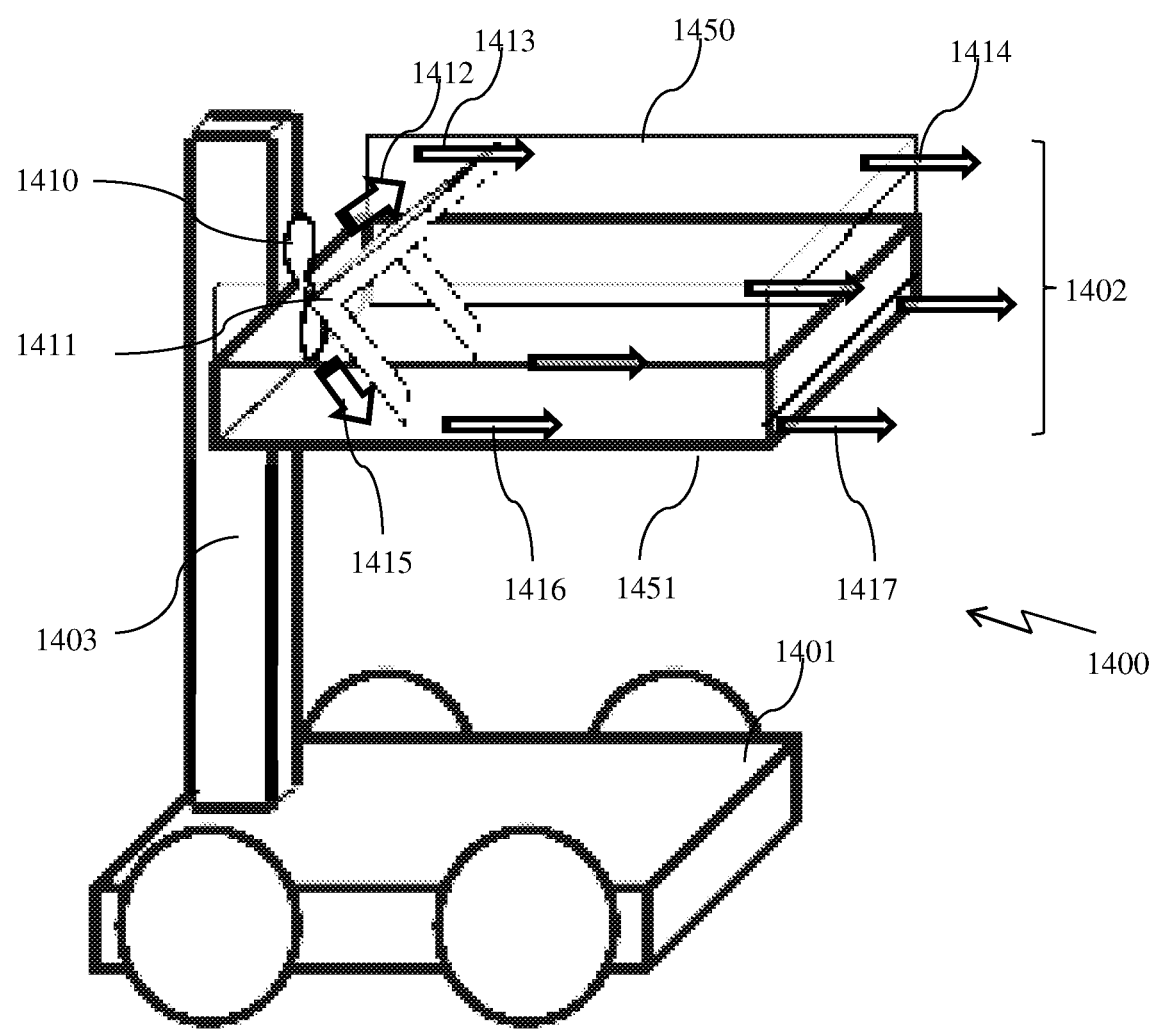
FIG. 9, schematically illustrating in non-limiting and out-of-scale manners an MTI (1400) according to an embodiment of the invention.

Reference is now made to FIG. 9, schematically illustrating in non-limiting and out-of-scale manner an MTI (1400) according to an embodiment of the invention. MTI (1400) comprises, inter alia, transporting base platform (1401), incubating module (1402), a hood (1450) and a support pillar interconnecting the same (1403). The presents means and methods according to one embodiment of the invention for imaging a premature infant in an independently thermo-regulated gear, including independently thermo-regulated MRI (IT-MRI), independently thermo-regulated neonate's incubator (ITNI).

The incubator is an ITNI type, comprising a venting/heating modules (1410) flowing filtered humidified air towards a baffle (1411). This air flow (1412) is streamed upwardly (1413) and downwardly (1415) and leaves the incubator via a horizontal linear silent flow at opposite side (flow 1414 and 1417, respectively). It is in the scope of the invention wherein MTI 1400 is adapted by size and shape to introduce ITNI (1402) within an open bored MRI. Additionally or alternatively, the ANTI comprising a TRV can be incorporated in a trolley as depicted in IL Pat. Appl. 226488, filed 21 May 2013, titled: "A CRADLE FOR NEONATES", of which is hereby incorporated by reference in its entirety.

Figure 10:
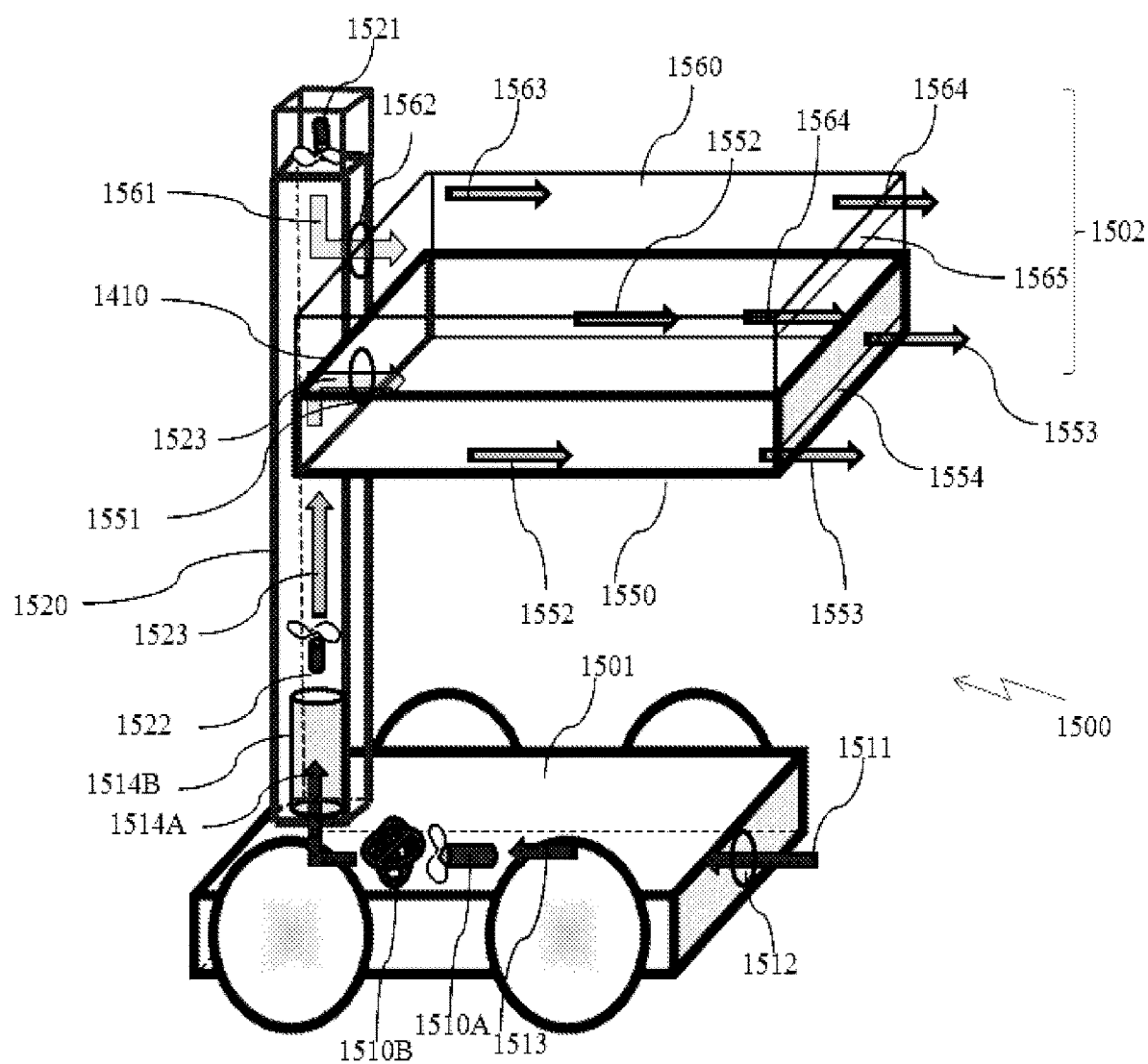
FIG. 10, schematically illustrating in non-limiting and out-of-scale manners an MTI (1500) according to an embodiment of the invention.

Reference is now made to FIG. 10, schematically illustrating in non-limiting and out-of-scale manners an MTI (1500) according to an embodiment of the invention. MTI (1500) comprises, inter alia, transporting platform (1501), incubating module (1502) and a support interconnecting the same (1520). The incubator is an ITNI type, comprising one or more venting/heating modules flowing filtered, humidified air towards the ITNI.

According to one embodiment of the invention, ITNI (1502) comprises a proximal portion interconnected to support (1520) and a distal portion. ITNI further comprises base-less lower portion (1550) and a maneuverably open/close canopy-like upper portion (1560). In ITNI's proximal end, one or more apertures are provided at upper and lower portions (1562, 1551, respectively). Likewise, in ITNI's distal end, one or more apertures are provided at upper and lower portions (1565, 1554, respectively).

According to yet another embodiment of the invention, one or more upper thermo-regulating modules (1521) located e.g., on support (1520) are provided for venting, heating, humidifying and filtering ambient air and flowing it (flow 1561) via upper proximal aperture (1562), upper zone in the canopy (1563) and via upper aperture 1565 by exit flow (1564). Additionally or alternatively, one or more lower thermo-regulating modules (1522) located e.g., on support (1520) are provided for venting, heating, humidifying and filtering ambient air and flowing it (flow 1523) via lower proximal aperture (1551), lower zone of the incubator (1552) and via lower aperture 1554 by exit flow (1553). Additionally or alternatively, one or more lower thermo-regulating modules (1510A) which may comprise a vent (1510A), a heater (1510B), noise and/or heat isolating tubing and envelopes (1514B) located e.g., in transporting platform (1501) are provided for venting, heating, humidifying and filtering ambient air and flowing it from ambient external environment (flow 1511), via the platform (1501) (flow 1513) via the support (1520) (flow 1514A, 1523 and 1523), via lower proximal aperture (1551), lower zone of the incubator (1552) and via lower aperture 1554 by exit flow (1553). It is further in the scope of the invention wherein a combination of one or more of the following modules 1510, 1522 and 1521 and baffle 1411 (See FIG. 10) is utilized.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein at least one of the following holds true: (a) the TRV is a module selected from a group consisting of at least one first venting module, at least one first heating/cooling module, at least one filter located adjacently to either the first venting module or the first heating/cooling module and any combination thereof; (b) the TRV comprises at least one venting module configured to introduce air selected from a group consisting of: heated air, cooled air, humidified air, filtered air, room temperature air, predetermined gas concentrated air, air, and any combination thereof, into the ANTI; (c) the TRV comprises a feedback mechanism for the air quality selected from a group consisting of: temperature, humidity, pressure, airborne particle content, gas concentration, and any combination thereof, configured to maintain the quality in a predetermined value or value range; and, (d) the TRV is a fan, having at least one rotor rotating perpendicularly to a rotor's shaft, and further wherein the shaft is positioned in parallel to the ANTI's main longitudinal axis.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein the ANTI additionally comprising air turbulating means (ATM) for slowing and moderating the airflow stream; further wherein at least one of the following is held true: (a) the ANTI comprising at least one first TRV located in one of the ends and at least one second TRV located in the opposite end; (b) the at least one TRV is located within the ANTI; (c) the at least one TRV is located outside the ANTI and is in air communication with the ANTI by means of a tubing; (d) at least one TRV is in air communication with the ANTI, and at least one TRV is located remotely from the ANTI. According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein the ANTI is in air communication with at least one air recycling mechanism (ARM); the ARM comprising: (a) at least one air inlet for collecting air stream from the ANTI's outer environment; (b) at least one recycled-air outlet for collecting air streamed from the ANTI's inner environment; and (c) at least one air inlet introducing air towards the ANTI's inner environment through the TRV; further wherein the ANTI additionally comprising at least one air flow regulator for regulating at least one air stream selected from a group consisting of: the recycled air stream, the air stream from the ANTI's outer environment, the air streamed towards the ANTI's inner environment, and any combination thereof.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein at least one of the following holds true: (a) the TRV is a module selected from a group consisting of at least one first venting module, at least one first heating/cooling module, at least one filter located adjacently to either the first venting module or the first heating/cooling module and any combination thereof; (b) the TRV comprises at least one venting module configured to introduce air selected from a group consisting of: heated air, cooled air, humidified air, filtered air, room temperature air, predetermined gas concentrated air, air, and any combination thereof, into the ANTI; (c) the TRV comprises a feedback mechanism for the air quality selected from a group consisting of: temperature, humidity, pressure, airborne particle content, gas concentration, and any combination thereof, configured to maintain the quality in a predetermined value or value range; and, (d) the TRV is a fan, having at least one rotor rotating perpendicularly to a rotor's shaft, and further wherein the shaft is positioned in parallel to the ANTI's main longitudinal axis; further wherein the ANTI having a cross section perpendicular to the main longitudinal axis with a central portion and a peripheral portion, located adjacent to the ANTI's walls; wherein the ANTI further comprising at least one air baffler located at least one position, the position is selected from a group consisting of: the one end, being either proximal or distal, the opposite end, and any combination thereof; the at least one air baffler is positioned within the ANTI at or adjacent to the ANTI's central portion thereby providing between the baffler and the walls apertures for the air to flow along the main longitudinal axis.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein at least one of the following holds true: (a) the TRV is a module selected from a group consisting of at least one first venting module, at least one first heating/cooling module, at least one filter located adjacently to either the first venting module or the first heating/cooling module and any combination thereof; (b) the TRV comprises at least one venting module configured to introduce air selected from a group consisting of: heated air, cooled air, humidified air, filtered air, room temperature air, predetermined gas concentrated air, air, and any combination thereof, into the ANTI; (c) the TRV comprises a feedback mechanism for the air quality selected from a group consisting of: temperature, humidity, pressure, airborne particle content, gas concentration, and any combination thereof, configured to maintain the quality in a predetermined value or value range; and, (d) the TRV is a fan, having at least one rotor rotating perpendicularly to a rotor's shaft, and further wherein the shaft is positioned in parallel to the ANTI's main longitudinal axis; further wherein at least one of the following holds true: (a) the ANTI, the TRV or both comprises at least one air filter; and, (b) the ANTI comprising at least one air channel, configured to direct the airflow within the ANTI; further wherein at least one of the following holds true: (a) the ANTI is configured to direct the airflow drift to bypass the location of the neonate residing within; (b) the ANTI is configured to have an air flow of X per volume W and time Y; (c) the ANTI is configured to have an air flow of X per volume W and time Y configurable by the user, auto regulated according to information received by at least one sensor, or both; and, (d) the ANTI is configured to provide linear air flow, turbulent air flow or both within at least a portion of the ANTI inner volume; further wherein the ANTI, comprising sound attenuating means configured to at least partially attenuate a selected from a group consisting of: the sounds generated by an MRD, the sound generated by the TRV, the sound of air movement within the ANTI, and any combination thereof; further wherein at least one of the following holds true: (a) the ANTI, the TRV or both comprising connections configured to at least partially absorb vibration; and, (b) the ANTI is connected to the TRV by flexible vibration absorptive materials, connectors or both;

further wherein the ANTI, the TRV or both are connected to externally supplied pressurized gas.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein at least one of the following holds true: (a) the TRV is a module selected from a group consisting of at least one first venting module, at least one first heating/cooling module, at least one filter located adjacently to either the first venting module or the first heating/cooling module and any combination thereof; (b) the TRV comprises at least one venting module configured to introduce air selected from a group consisting of: heated air, cooled air, humidified air, filtered air, room temperature air, predetermined gas concentrated air, air, and any combination thereof, into the ANTI; (c) the TRV comprises a feedback mechanism for the air quality selected from a group consisting of: temperature, humidity, pressure, airborne particle content, gas concentration, and any combination thereof, configured to maintain the quality in a predetermined value or value range; and, (d) the TRV is a fan, having at least one rotor rotating perpendicularly to a rotor's shaft, and further wherein the shaft is positioned in parallel to the ANTI's main longitudinal axis; further wherein at least a portion of the ANTI's walls are double jacket walls arrangement (DJW); the DJW comprising a perforated inner-wall and an intact non-perforated outer-wall, thereby the DJW facilitating the air stream, along the main longitudinal axis in a conduit having a predefined width (w) and length (l); further wherein at least one of the following holds true: (a) the width and the length (w, l) are equal along the longitudinal axis, are changed along the longitudinal axis or any combination thereof along the longitudinal axis; and, (b) the conduit between the double jacket walls comprises a selected from a group consisting of: sound attenuating means, thermal isolating materials, vibration reducing means, RF coils, conductive material, non-conductive material, and any combination thereof; further wherein at least one portion of the ANTI along the longitudinal axis, the width (W) in ANTI's upper wall is $W_1$ in its proximal side, $W_2$ in its distal side, and in ANTI's lower wall the width is $W_3$ in its proximal side, $W_4$ in its distal side; at least one of the following is held true: (a) $W_1$ is larger than $W_2$ and $W_3$ is larger than $W_4$; (b) $W_1$ is larger than $W_2$ and $W_3$ is smaller than $W_4$; (C) $W_1$ is smaller than $W_2$ and $W_3$ is smaller than $W_4$; (d) $W_1$ is smaller than $W_2$ and $W_3$ is larger than $W_4$; (e) $W_1$ is larger than $W_3$ and $W_2$ is larger than $W_4$; (f) $W_1$ is larger than $W_3$ and $W_2$ is smaller than $W_4$; (g) $W_1$ is smaller than $W_3$ and $W_2$ is smaller than $W_4$; and, (h) $W_1$ is smaller than $W_3$ and $W_2$ is larger than $W_4$.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein at least a portion of the ANTI, the TRV or both are made of MRI-safe materials; further wherein the ANTI comprises a central processing unit (CPU) configured to a selected from a group consisting of: control the TRV, control the TRV by responding to signals received from at least one sensor, control the TRV according to values defined by the user, control the TRV according to predefined physical condition of the neonate, and any combination thereof.

According to one embodiment of the invention an elongated active thermo-regulated neonatal transport incubator (ANTI), having a main longitudinal axis with a proximal end and an opposite distal end comprising adjacent to at least one of the ends a temperature regulating vent (TRV), wherein the TRV is configured to stream air from one end towards the opposite end substantially along the axis; further wherein the ANTI is configured, by means of size and shape, to accommodate the neonate in parallel to the axis; further wherein at least a portion of the ANTI is configured by means of size and shape to be inserted into an MRD having an open bore in its longitudinal axis; further wherein the ANTI is configured to accommodate the neonate parallel to the MRD bore; further wherein at least one of the following holds true: (a) the ANTI comprises at least one aperture configured to be reversibly opened/closed; and, (b) the ANTI is permeable to radiation selected from a group consisting of alpha, beta, gamma, x-ray, magnetic, ionizing, thermal, infrared, sound, and any combination thereof; further wherein the ANTI is interconnected to a mobile base by at least one support, to form a mobile thermo-regulated transport incubator (MTI); further wherein at least one of the following holds true: (a) the mobile base and at least one support are made of MRI safe material; (b) the MTI is configured to be at least partially inserted within an MRD bore; and, (c) the TRV is comprised of at least one venting module located at a selected from a group consisting of: the mobile base, the at least one support, the at least one ANTI end, and any combination thereof; further wherein the venting module is connected to the ANTI by at least one tubing. Reference is now made to FIG. 11A-E, which illustrate in an out of scale manner a set of incubators (100a-100d) for thermo-regulating a neonate (1). The incubators comprising, inter alia, a hood (1450) for accommodating a neonate (1). The hood is provided in any shape, such as a polygonal or an ellipsoid shape, and it is constructed of one, two or more layers, each of which is made of any suitable material, such as a polymeric composition (PMMA, PVC, polycarbonate etc.) glass, metal, foam or a mixture thereof. The hood is mounted on a base portion (1020) which enables streaming of thermo-regulated air (160) from an air-thermo-regulating vent (TRV) (101) to the hood (1450). The hood may be reversibly detachable from the base or permanently attached to it. The flow of the thermo-regulated air (160) in the base is facilitated towards the hood through an array of a texturize perforations (170) provided at least on a portion of floor, side walls of the hood or a combination thereof. It is in the scope of the invention wherein at least a portion of the the perforations is either of a permanent shape or is adjustably and/or is maneuverable and/or regulateable in a feed-backed manner for directing and/or regulating (e.g., slowing, moderating, etc.) the airflow stream. It is further in the scope of the invention wherein at least a portion of the perforations is for unidirectional air flow or bidirectional air flow. It is further is in the scope of the invention wherein air flow is carried out through at least one conduit, such as a noise/thermo-isolated pipe, in an air communication with the base on which the hood is mounted. It is further is in the scope of the invention wherein the Thermo-regulated air streams into the base from at least one TRV (101) which is located outside and remotely form the base (1020) thereby reducing the vibration and noise results from the vent operation and the stream of the air. The TRV is locatable thus in one or more of different locations outside the incubator's hood (1450) and outside and removably from the base (1020).

It is further is in the scope of the invention wherein the TRV comprises or is in connection with at least one venting module, (e.g., a fan, a jet, a blower, a compressor, a fluid pump, a peltier module etc.). It is further is in the scope of the invention wherein the TRV comprises or is in connection with at least one heating/cooling module (e.g., an air conditioned system, an infrared heater, a water/oil-heated radiator, an electric coil-like heater, an open coil air heater, a round open coil air heater, a convection heater, straight or formed tubular heaters, a quartz tube air heater, a capacitor-type heater, a Pelletier module or any combination of the same). It is further is in the scope of the invention wherein the TRV comprises or is in connection with at least one air humidification module. It is further is in the scope of the invention wherein the TRV comprises or is in connection with at least one air filtering module. It is further is in the scope of the invention wherein the TRV comprises or is in connection with at least one air deionizing module. It is further is in the scope of the invention wherein the TRV comprises or is in connection with at least one air-turbulating module for slowing or adjusting or gentling air flow characteristics. The air-turbulating means are selected in a non-limiting manner from active members, such as fan, multiple-fan arrangement or cascade thereof, air pump, Dyson-type bladeless air multiplier, venting apparatus etc., and/or passive members, such as texturized strainer, curved conduits in a continuous barrier etc. It is further is in the scope of the invention wherein at least one TRV comprises one or more the above mentioned modules.

Reference is now made to FIG. 11A, which illustrates in an out of scale manner an embodiment of the incubator (100). Here, incubator comprises hood and base (1450, 1020, respectively) for accommodating a neonate. The incubator further comprises a cart (1400) to which it mounted by means of an erected supporting structure (170). In this embodiment, one or more TRVs (101) are positioned on the incubator's cart (1400). The air is streamed by means of the TRV(s) via the support (170) which have an open bore provided here as an air conduit, to base (1020). From the base, air flow is facilitated upwardly (160) to penetrate the hood or hood's inner double-wall jacket (not shown) throughout perforations (170).

It is acknowledged that it is in the scope of the invention wherein the incubator comprises or is in connection with a cart as shown as member 1400, and it also is in the scope of the invention wherein incubator does comprises nor is in connection with a cart. It is also acknowledged that it is in the scope of the invention wherein the incubator comprises or is in connection with a supporting member such as shown as member 170, and it also is in the scope of the invention wherein incubator does comprises nor is in connection with a supporting member.

Reference is now made to FIG. 11B, which illustrates in an out of scale manner an embodiment of an incubator (100a). Here, the incubator, which comprises a hood and a base, is in air connection with a supporting member 170. In one embodiment, TRV 101A is affixed within the lower portion of support 170 or is in connection with the lower portion, such that thermo-regulated air is streamed from the support, via the base to the hood. Additionally or alternatively, TRV 101B is affixed within the upper portion of support 170 or is in connection with the upper portion, such that thermo-regulated air is streamed from the support, via the base to the hood.

Reference is now made to FIG. 11C, which illustrates in an out of scale manner a side view of an embodiment of an incubator (100b). Here the incubator is a shown without support auxiliary and the cart auxiliary. Nevertheless, such auxiliaries are possible. Thermo-regulated air is produced in a remote location, here, a standalone TRV 101. Air is flown form a base to the hood via e.g., two different zones of perforation, here a foot-side perforation, and head-side perforation. At the middle portion of the incubator (1006b), thermo-regulated air is not streamed. The two portions (1006a) are interconnected by means of an air conduit (1006c). Reference is now made to FIG. 11D, which illustrates in an out of scale manner an embodiment of an incubator (100c). Here, an upper TRV (101) is streaming thermo-regulated air via the support (air inlet, $105_{in}$) throughout a thermo-isolating and noise-isolating pipe (151) such that e.g., the noise of the air flow turbulences within the support is not heard within the hood. Thermo-regulated air enters the base, and then enters the hood via predefined perforated zones (1006a). Base further comprises non-perforated area 1006B and air conduit (1006c). From the hood, outgoing air streams ($105_{out}$) are evacuated by a turbo-like mechanism, air-circulation regulator etc.

Reference is now made to FIG. 11E, which illustrates in an out of scale manner a face view cross-section an embodiment of an incubator (100b) further illustrated in FIG. 11C. Here, in FIG. 11E, thermo-regulated air (1006a) is streamed via the partially perforated floor and/or side walls in more than one direction, namely a clock-wise circulation of foot-side air (161), and counter-clock-wise circulation of head-side air (162) and vice versa.

Figures 11F, 11G:
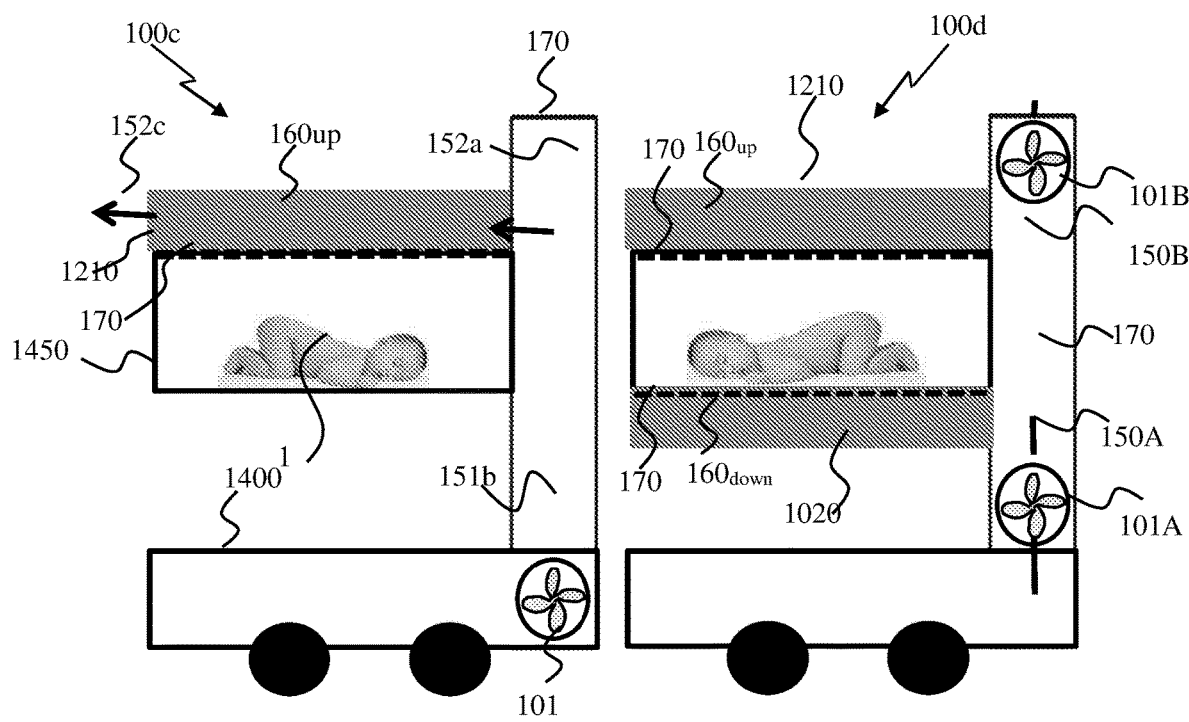
FIG. 11F illustrating in an out of scale manner a side view of a neonate (1) incubator.
FIG. 11G illustrating in an out of scale manner a side view of a neonate (1) incubator; and, FIG. 12 illustrating a schematic flow diagram of the method for thermo-regulating an incubator (200).

Reference is now made to FIGS. 11F and 11G, which illustrate in an out of scale manner a side view of a set of a few neonate (1) incubators (100c, 100d) according to yet another embodiment of the invention. Incubator 100c is a base-less incubator, comprising at least one TRV (101) for supplying an effective measure of thermo-regulated air to incubator's hood (1450). In this embodiment, TRV is located in incubator's cart (1400), and streams thermo-regulated air (151b) via support's (170) open bore. Pre-treated air is provided by air inlet (152a), here an upper air inlet which prevents dust and other contamination influx. Thermo-regulated air flow is facilitated towards hood 1450 via canopy (1210). The canopy comprises various air inlets and outlets, such as thermo-regulated air inlet, a plurality of apertures within perforated ceiling wall (170), and optionally excess-air exit for outflow of excess air when hood-air is circulated. It is in the scope of the invention that one or more TRVs are located in the cart (1400) or adjacent to the same as shown at FIG. 11F, within or adjacent to the support lower portion as shown in FIG. 11B, within or adjacent to the support's upper portion (FIG. 11B), above the canopy as illustrated in FIG. 11D, in a remote location as presented in FIG. 11C, in a combination of the same or in any different location.

Reference is now made to FIG. 11G, which illustrates in an out of scale manner an incubator (100d) which comprises a base and a canopy. According to an embodiment of the invention, thermo-regulated air is provided by TRV (101B) which is located e.g., at the upper portion of the support (170). Thermo-regulated air ($160_{up}$) is directed downwards and/or downwards and sideward (e.g., clockwise and/or counter-clock-wise air streams) from the canopy, via at least one perforated zone (170), towards the hood. Then, air is flown downwards to a base and then it exits the incubator. In one embodiment of the invention, which may be implied and utilized in any of the aforesaid incubator and thermo-regulating systems, another vent, e.g., 101A which is located in the support's lower portion, is evacuating the air outgoing streams ($160_{out}$) via a perforated bottom-wall provided in the base (1020), to vacuum air stream 150A outside the incubator air system.

Figure 12:
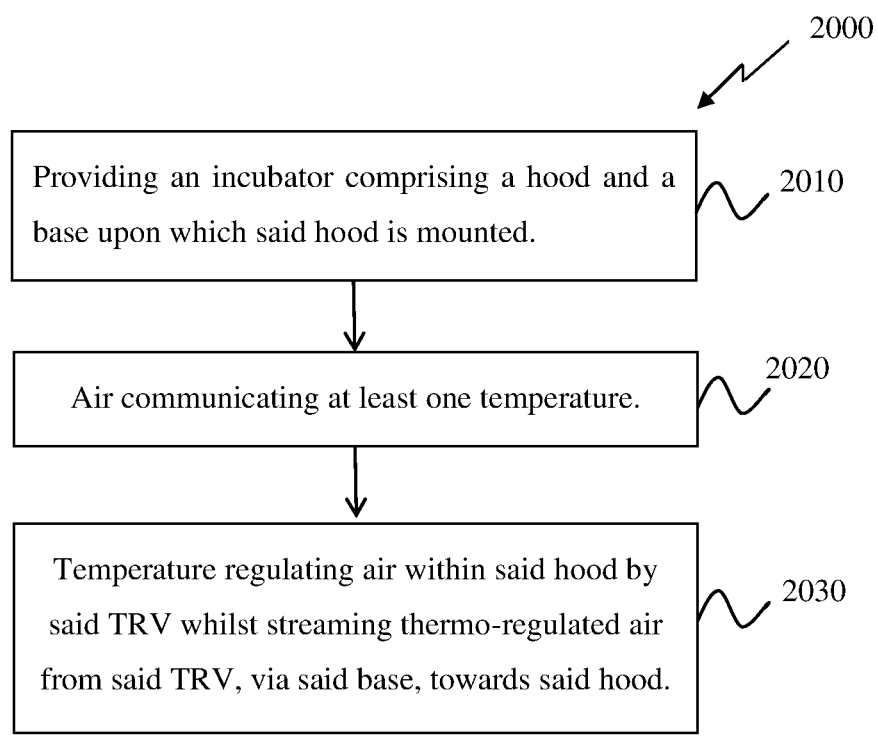

Reference is now made to FIG. 12, which is illustrating a schematic flow diagram of the method for thermo-regulating a neonate (2000). In the first step an incubator is obtained (2100). The obtained incubator is comprised of a hood to which the neonate is accommodated and a base on which the hood is mounted. The next step includes air communicating a TRV to the base (2200) in a way that thermo-regulated air produced by the TRV is streamed to the base. In one embodiment, air communicating is done through at least one conduit connecting the TRV with the base. The conduit may contain means for actively pushing air through the conduit or that air passively flows through the conduit. The conduit may be of similar width all along its length or the width may change in order to improve the flow. In the last step, the hood is being thermo-regulated (2300) by the TRV through the base. Once the hood reaches the desired temperature a neonate can be introduced into it.

The invention claimed is:

1. An elongated active thermo-regulated neonatal transportable incubator (ANTI), having a main longitudinal axis with a proximal end and an opposite distal end, said ANTI comprising:
   a temperature regulating vent (TRV) adjacent to at least one of said ends and including an air moving device for generating a stream of air, said air moving device having an output, wherein the stream of air at the output of the air moving device is substantially parallel to the main longitudinal axis and directed from one end towards the opposite end within said ANTI; and
   at least one air recycling mechanism (ARM) for recycling air from said opposite end to said TRV, said ARM comprising a tube connecting between said opposite end and said TRV, said tube comprising an opening for drawing fresh air from the surroundings of the ANTI, wherein said tube further comprises an air flow regulator for controlling a ratio between the amounts of recycled air and fresh air flowing into the ANTI,
   wherein the ANTI is closable such that when closed, at least one portion of said ANTI is dimensioned to fit an open bore of a magnetic resonance device (MRD) comprising permanent magnet installations with main magnets stationed above and below a patient location in the bore.

2. The ANTI of claim 1, wherein the at least one portion of the ANTI that is dimensioned to fit the open bore of the MRD includes the TRV.

3. The ANTI of claim 1, further comprising at least one second TRV located in said opposite end.

4. The ANTI of claim 1, wherein the cross sectional area of the ANTI includes a central portion and a peripheral portion each portion extending the length of said main longitudinal axis, the peripheral portion being located adjacent to walls of the ANTI and surrounding the central portion, the ANTI further comprising:
   a neonate location configured for placement of a neonate; and
   at least one air baffler located within said ANTI at said central portion leaving one or more apertures between said baffler and said walls thereby forcing air to flow in a linear manner and parallel to said main longitudinal axis and to bypass the location of said neonate residing within, wherein the structure of said at least one baffler is noncontiguous over the length of the neonate location.

5. The ANTI according to claim 1, wherein said ANTI comprises sound attenuating means to at least partially attenuate any one or more of sounds generated by a magnetic resonance device, the sound generated by said TRV, and the sound of air movement within said ANTI.

6. The ANTI according to claim 1, wherein said ANTI is connected to externally supplied pressurized gas.

7. The ANTI according to claim 1, wherein at least a portion of said ANTI comprises a double jacket walls arrangement (DJW); said DJW comprising a perforated inner-wall and an intact non-perforated outer-wall, to facilitate the streamed air along said main longitudinal axis in a conduit having a predefined width (w) and length (l).

8. The ANTI according to claim 7, wherein at least one of said width and said length (w, l) change along said longitudinal axis thereby causing streamed air to be effluxed into the inner environment of the ANTI and air from the inner environment of the ANTI to be influxed into the conduit.

9. The ANTI according to claim 7, wherein said conduit comprises at least one of the following: a sound attenuating means, thermal isolating materials, a vibration reducing means, RF coils, conductive material and non-conductive material.

10. The ANTI according to claim 1, wherein at least a portion of said ANTI, said TRV or both are made of MRI-safe materials.

11. The ANTI according to claim 1, wherein said ANTI comprises a central processing unit (CPU) to control said TRV by responding to signals received from at least one sensor, according to values defined by the user, according to predefined physical condition of said neonate, or any combination thereof.

12. The ANTI according to claim 1, wherein said ANTI is permeable to one or more of alpha radiation, beta radiation, gamma radiation, x-ray radiation, magnetic fields, ionizing radiation, thermal radiation, and infrared radiation.

13. The ANTI according to claim 1, wherein said ANTI is interconnected to a mobile base by at least one support post, to form a mobile thermo-regulated transportable incubator (MTI).

14. The ANTI according to claim 13, wherein-said mobile base is made of MRI safe materials and wherein said MTI is configured to be at least partially inserted within a magnetic resonance device bore.

15. The ANTI of according to claim 1, wherein the TRV further comprises a heating/cooling module and wherein said ANTI further comprising at least one filter located adjacently to either said air moving device or said heating/cooling module.

16. The ANTI according to claim 1, wherein the stream of air from the output of the air moving device to the opposite end is substantially parallel to the main longitudinal axis.

* * * * *